(12) United States Patent
Miller et al.

(10) Patent No.: US 7,307,093 B2
(45) Date of Patent: Dec. 11, 2007

(54) THIAZOLIDINONE AMIDES, THIAZOLIDINE CARBOXYLIC ACID AMIDES, METHODS OF MAKING, AND USES THEREOF

(75) Inventors: Duane D. Miller, Germantown, TN (US); Veeresa Gududuru, Memphis, TN (US); James T. Dalton, Columbus, OH (US); Eunju Hurh, Columbus, OH (US)

(73) Assignees: The University of Tennessee Research Foundation, Memphis, TN (US); Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 10/992,175

(22) Filed: Nov. 18, 2004

(65) Prior Publication Data

US 2006/0040998 A1   Feb. 23, 2006

Related U.S. Application Data

(60) Provisional application No. 60/523,079, filed on Nov. 18, 2003.

(51) Int. Cl.
*A61K 31/426* (2006.01)
*A61K 31/427* (2006.01)
*C07D 277/02* (2006.01)

(52) U.S. Cl. .................................. 514/365; 548/200
(58) Field of Classification Search ................ 548/200; 514/365
See application file for complete search history.

(56) References Cited

U.S. PATENT DOCUMENTS

2006/0014740 A1   1/2006   Miller et al.

FOREIGN PATENT DOCUMENTS

EP   0 279 681 A2   8/1988
RU   2139283 C1   10/1999
RU   97114846 A   11/1999

OTHER PUBLICATIONS

STN search report: Pavlova et al. Khimiko-Farmatsevticheskii Zhurnal (1986), 20(9), 1083-8.*
Holmes et al., "Reagents for Combinatorial Organic Synthesis: Development of a New o-Nitrobenzyl Photolabile Linker for Solid Phase Synthesis," *J. Org. Chem.* 60:2318-2319 (1995).

* cited by examiner

*Primary Examiner*—Kamal A. Saeed
*Assistant Examiner*—Yong Chu
(74) *Attorney, Agent, or Firm*—Nixon Peabody LLP

(57) ABSTRACT

Substituted thiazolidinone carboxylic acid amides and substituted thiazolidine carboxylic acid amides according to formulae (I) and (II) are disclosed

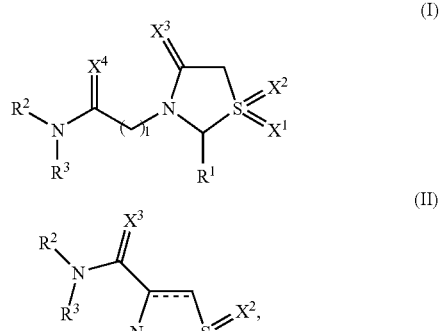

where the various substituent groups are as defined in the specification. Methods of making these compounds, pharmaceutical compositions containing the compounds, and their use, particularly for treating or preventing cancer, are also disclosed.

13 Claims, 6 Drawing Sheets

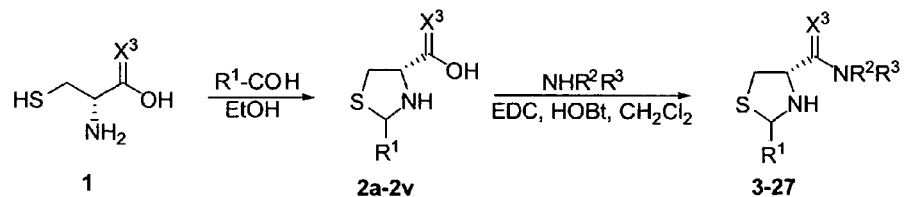

(Scheme 1)

| Intermediate Compound | R¹ | X³ | R² | R³ | Final Compound |
|---|---|---|---|---|---|
| 2a | phenyl | O | H | C7 alkyl | 3 |
| 2a | phenyl | O | H | C14 alkyl | 4 |
| 2a | phenyl | O | H | C18 alkyl | 5 |
| 2a | phenyl | O | H | C19 alkyl | 6 |
| 2b | n-dodecyl | O | H | C18 alkyl | 7 |
| 2c | cycohexyl | O | H | C18 alkyl | 8 |
| 2d | benzyl | O | H | C18 alkyl | 9 |
| 2e | 3-indolyl | O | H | C18 alkyl | 10 |
| 2f | 3-pyridinyl | O | H | C18 alkyl | 11 |
| 2g | 3-furanyl | O | H | C18 alkyl | 12 |
| 2h | 4-dimethyl amino phenyl | O | H | C18 alkyl | 13 |
| 2i | 3-hydroxyphenyl | O | H | C18 alkyl | 14 |
| 2j | 4-methoxyphenyl | O | H | C18 alkyl | 15 |
| 2k | 3,4-dimethoxyphenyl | O | H | C18 alkyl | 16 |
| 2l | 3,4,5-trimethoxyphenyl | O | H | C18 alkyl | 17 |
| 2m | 4-acetylamino phenyl | O | H | C18 alkyl | 18 |
| 2n | 4-fluorophenyl | O | H | C18 alkyl | 19 |
| 2o | 4-bromophenyl | O | H | C18 alkyl | 20 |
| 2p | 4-nitrophenyl | O | H | C18 alkyl | 21 |
| 2q | 4-cyanophenyl | O | H | C18 alkyl | 22 |
| 2r | 3,5-difluorophenyl | O | H | C18 alkyl | 23 |
| 2s | 2,6-dichlorophenyl | O | H | C18 alkyl | 24 |
| 2t | 3-bromo-4-fluorophenyl | O | H | C18 alkyl | 25 |
| 2u | 4-methylphenyl | O | H | C18 alkyl | 26 |
| 2v | biphenyl | O | H | C18 alkyl | 27 |

Figure 1

(Scheme 2)

(Scheme 3)

(Scheme 4)

(Scheme 5)

(Scheme 6)

THIAZOLIDINONE AMIDES, THIAZOLIDINE CARBOXYLIC ACID AMIDES, METHODS OF MAKING, AND USES THEREOF

The present invention claims the priority benefit of provisional U.S. Patent Application Ser. No. 60/523,079, filed Nov. 18, 2003, which is hereby incorporated by reference in its entirety.

This application was made, at least in part, with funding received from the U.S. Department of Defense under grant DAMD 17-01-1-0830. The U.S. government may retain certain rights in this invention.

FIELD OF THE INVENTION

The present invention relates to novel thiazolidinone amides, novel thiazolidine carboxylic acid amides, methods of making these compounds, and uses thereof, particularly for treating various cancers including but not limited to prostate, breast, and ovarian cancers.

BACKGROUND OF THE INVENTION

Prostate cancer accounts for 33% of all newly diagnosed malignancies among men in the United States (American Cancer Society: *Cancer Facts and Figures* (2003)). According to the American Cancer Society, an estimated 230,110 men will be diagnosed with prostate cancer in 2004, and 29,900 men will die of it (American Cancer Society: *Cancer Facts and Figures* (2004)). The incidence of prostate cancer varies worldwide, with the highest rates found in the United States, Canada, and Scandinavia, and the lowest rates found in China and other parts of Asia (Quinn and Babb, "Patterns and Trends in Prostate Cancer Incidence, Survival, Prevalence and Mortality. Part: International Comparisons," *BJU Int.* 90:162-173 (2002); Gronberg, "Prostate Cancer Epidemiology," *Lancet* 361:859-864 (2003)). These differences are caused by genetic susceptibility, exposure to unknown external risk factors, differences in health care and cancer registration, or a combination of these factors.

Cancer of the prostate is multifocal and it is commonly observed that the cancerous gland contains multiple independent lesions, suggesting the heterogeneity of the disease (Foster et al., "Cellular and Molecular Pathology of Prostate Cancer Precursors," *Scand. J. Urol. Nephrol.* 205:19-43 (2000)). Determinants responsible for the pathologic growth of the prostate remain poorly understood, although steroidal androgens and peptide growth factors have been implicated (Agus et al., "Prostate Cancer Cell Cycle Regulators: Response to Androgen Withdrawal and Development of Androgen Independence," *J. Natl. Cancer. Inst.* 91:1869-1876 (1999); Djakiew, "Dysregulated Expression of Growth Factors and Their Receptors in the Development of Prostate Cancer," *Prostate* 42:150-160 (2000)). As long as the cancer is confined to the prostate, it can be successfully controlled by surgery or radiation, but in metastatic disease, few options are available beyond androgen ablation (Frydenberg et al., "Prostate Cancer Diagnosis and Management," *Lancet* 349:1681-1687 (1997)), the mainstay of treatment in the case of lymph node involvement or disseminated loci. Once tumor cells have become hormone refractory, the standard cytotoxic agents are marginally effective in slowing disease progression, although they do provide some degree of palliative relief. Current chemotherapeutic regimens, typically two or more agents, afford response rates in the range of only 20-30% (Beedassy et al., "Chemotherapy in Advanced Prostate Cancer," *Sem. Oncol.* 26:428-438 (1999); Raghavan et al., "Evolving Strategies of Cytotoxic Chemotherapy for Advanced Prostate Cancer," *Eur. J. Cancer* 33:566-574 (1997)).

One promising drug development strategy for prostate cancer involves identifying and testing agents that interfere with growth factors and other molecules involved in the cancer cell's signaling pathways. G-protein coupled receptors ("GPCRs") are a family of membrane-bound proteins that are involved in the proliferation and survival of prostate cancer cells initiated by binding of lysophospholipids ("LPLs") (Raj et al., "Guanosine Phosphate Binding Protein Coupled Receptors in Prostate Cancer: A Review," *J. Urol.* 167:1458-1463 (2002); Kue et al., "Essential Role for G Proteins in Prostate Cancer Cell Growth and Signaling," *J. Urol.* 164:2162-2167 (2000); Guo et al., "Mitogenic Signaling in Androgen Sensitive and Insensitive Prostate Cancer Cell Lines," *J. Urol.* 163:1027-1032 (2000); Barki-Harrington et al., "Bradykinin Induced Mitogenesis of Androgen Independent Prostate Cancer Cells," *J. Urol.* 165:2121-2125 (2001)). The importance of G protein-dependent pathways in the regulation of growth and metastasis in vivo is corroborated by the observation that the growth of androgen-independent prostate cancer cells in mice is attenuated by treatment with pertussis toxin, an inhibitor of Gi/o proteins (Bex et al., "Influence of Pertussis Toxin on Local Progression and Metastasis After Orthotopic hnplantation of the Human Prostate Cancer Cell Line PC3 in Nude Mice," *Prostate Cancer Prostatic Dis.* 2:36-40 (1999)). Lysophosphatidic acid ("LPA") and sphingosine 1-phosphate ("S1P") are lipid mediators generated via the regulated breakdown of membrane phospholipids that are known to stimulate GPCR-signaling.

LPL binds to GPCRs encoded by the Edg gene family, collectively referred to as LPL receptors, to exert diverse biological effects. LPA stimulates phospholipase D activity and PC-3 prostate cell proliferation (Qi et al., "Lysophosphatidic Acid Stimulates Phospholipase D Activity and Cell Proliferation in PC-3 Human Prostate Cancer Cells," *J. Cell. Physiol.* 174:261-272 (1998)). Further, prior studies have shown that LPA is mitogenic in prostate cancer cells and that PC-3 and DU-145 express $LPA_1$, $LPA_2$, and $LPA_3$ receptors (Daaka, "Mitogenic Action of LPA in Prostate," *Biochim. Biophys. Acta.* 1582:265-269 (2002)). Advanced prostate cancers express LPL receptors and depend on phosphatidylinositol 3-kinase ("PI3K") signaling for growth and progression to androgen independence (Kue and Daaka, "Essential Role for G Proteins in Prostate Cancer Cell Growth and Signaling," *J. Urol.* 164:2162-2167 (2000)). Thus, these pathways are widely viewed as one of the most promising new approaches to cancer therapy (Vivanco et al., "The Phosphatidylinositol 3-Kinase AKT Pathway in Human Cancer," *Nat. Rev. Cancer* 2:489-501 (2002)) and provide an especially novel approach to the treatment of advanced, androgen-refractory prostate cancer. Despite the promise of this approach, there are no clinically available therapies that selectively exploit or inhibit LPA or PI3K signaling.

The present invention is directed to overcoming these and other deficiencies in the prior art.

SUMMARY OF THE INVENTION

A first aspect of the present invention relates to compounds according to formula (I) and formula (II)

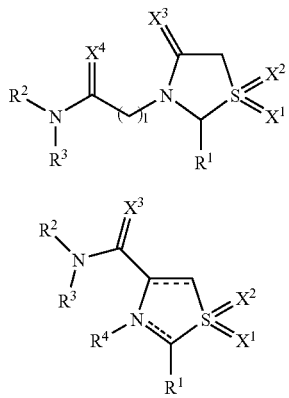

wherein
  $X^1$ and $X^2$ are each optional, and each can be oxygen;
  $X^3$ and $X^4$ are each optional, and each can be oxygen or sulfur;
  l is an integer from 1 to 12;
  $R^1$ is selected from the group of saturated or unsaturated cyclic hydrocarbons, saturated or unsaturated N-heterocycles, saturated or unsaturated O-heterocycles, saturated or unsaturated S-heterocycles, saturated or unsaturated mixed heterocycles, aliphatic or non-aliphatic straight- or branched-chain C1 to C30 hydrocarbons, or

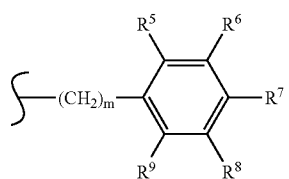

or —$(CH_2)_m$—$Y^1$ where m is an integer from 0 to 10 and $Y^1$ is a saturated or unsaturated cyclic hydrocarbon, saturated or unsaturated N-heterocycle, saturated or unsaturated O-heterocycle, saturated or unsaturated S-heterocycle, or saturated or unsaturated mixed heterocycle;
  $R^2$ is hydrogen, an aliphatic or non-aliphatic straight- or branched-chain C1 to C30 hydrocarbon, $R^{10}$—N(Z)-hydrocarbon- or $R^{10}$-hydrocarbon- where the hydrocarbon group is an aliphatic or non-aliphatic straight- or branched-chain C1 to C30 hydrocarbon, a saturated or unsaturated cyclic hydrocarbon, a saturated or unsaturated N-heterocycle, a saturated or unsaturated O-heterocycle, a saturated or unsaturated S-heterocycle, a saturated or unsaturated mixed heterocycle, or

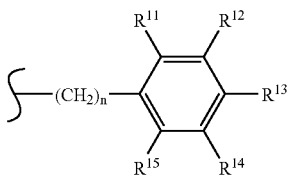

or —$(CH_2)_n$—$Y^2$ where n is an integer from 0 to 10 and $Y^2$ is a saturated or unsaturated cyclic hydrocarbon, saturated or unsaturated N-heterocycle, saturated or unsaturated O-heterocycle, saturated or unsaturated S-heterocycle, or saturated or unsaturated mixed heterocycle;
  $R^3$ is hydrogen or an aliphatic or non-aliphatic straight- or branched-chain C1 to C10 hydrocarbon;
  $R^4$ is optional, or can be hydrogen, an aliphatic or non-aliphatic straight- or branched-chain C1 to C10 hydrocarbon, acyl, acetyl, or mesyl;
  $R^5$, $R^6$, $R^7$, $R^8$, $R^9$, $R^{11}$, $R^{12}$, $R^{13}$, $R^{14}$, and $R^{15}$ are independently selected from the group of hydrogen, hydroxyl, an aliphatic or non-aliphatic straight- or branched-chain C1 to C10 hydrocarbon, alkoxy, aryloxy, nitro, cyano, chloro, fluoro, bromo, iodo, haloalkyl, dihaloalkyl, trihaloalkyl, amino, alkylamino, dialkylamino, acylamino, arylamino, amido, alkylamido, dialkylamido, arylamido, aryl, C5 to C7 cycloalkyl, arylalkyl;
  $R^{10}$ is H(Z)N—, H(Z)N-hydrocarbon-, H(Z)N-hydrocarbon-N(Z)-hydrocarbon-, H(Z)N-hydrocarbon-O-hydrocarbon-, hydrocarbon-O-hydrocarbon-, hydrocarbon-N(Z)-hydrocarbon-, H(Z)N-hydrocarbon-carbonyl-hydrocarbon-, hydrocarbon-carbonyl-hydrocarbon-, H(Z)N-phenyl-, H(Z)N-phenylalkyl-, H(Z)N-phenylalkyl-N(Z)-hydrocarbon-, H(Z)N-phenylalkyl-O-hydrocarbon-, phenylalkyl-O-hydrocarbon-, phenylalkyl-N(Z)-hydrocarbon-, H(Z)N-phenylalkyl-carbonyl-hydrocarbon-, or phenylalkyl-carbonyl-hydrocarbon-, wherein each hydrocarbon is independently an aliphatic or non-aliphatic straight- or branched-chain C1 to C10 group, and wherein each alkyl is a C1 to C10 alkyl; and
  Z is independently hydrogen or t-butoxycarbonyl.

A second aspect of the present invention relates to a pharmaceutical composition including a pharmaceutically acceptable carrier and a compound according to the first aspect of the present invention.

A third aspect of the present invention relates to a method of destroying a cancer cell that includes the steps of: providing a compound according to the first aspect of the present invention and contacting a cancer cell with the compound under conditions effective to destroy the contacted cancer cell.

A fourth aspect of the present invention relates to a method of treating or preventing a cancerous condition that includes the steps of: providing a compound according to the first aspect of the present invention and administering an amount of the compound to a patient in a manner effective to treat or prevent a cancerous condition.

A fifth aspect of the present invention relates to a method of making a compound according to formula (I) that includes the steps of: reacting an intermediate according to formula (III),

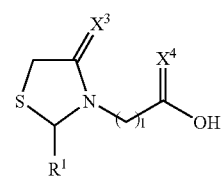

where l, $R^1$, $X^3$, and $X^4$ are defined as above, with either (i) a suitable primary or secondary amine according to the formula (HNR²R³) where R² and R³ are defined as above, or (ii) ammonia in the presence of an R²—H containing compound, under conditions effective to form the compound according to formula (I).

A sixth aspect of the present invention relates to a method of making a compound according to formula (II) that includes the steps of: reacting an intermediate according to formula (IV),

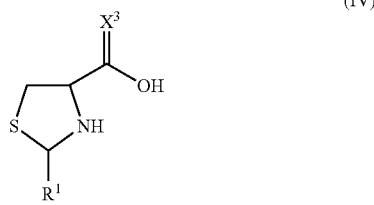

where R¹ and X³ are defined as above, with a primary or secondary amine according to the formula (HNR²R³) where R² and R³ are defined as above, under conditions effective to form the compound according to formula (II).

A seventh aspect of the present invention relates to intermediate compounds according to formula (III) and formula (IV).

The present invention affords a significant improvement over previously identified cancer therapeutics that are known to be useful for the inhibition of prostate cancer cell growth. In a previous report, it was shown that cytotoxic compounds were obtained by replacing the glycerol backbone in LPA with serine amide in five prostate cancer cell lines (Gududuru et al., "Synthesis and Biological Evaluation of Novel Cytotoxic Phospholipids for Prostate Cancer," *Bioorg. Med. Chem. Lett.* 14:4919-4923 (2004), which is hereby incorporated by reference in its entirety). The most potent compounds reported in Gududuru et al. (cited above) were non-selective and potently killed both prostate cancer and control cell lines. The present invention affords compounds that possess similar or even improved potency, but more importantly, improved selectivity, particularly with respect to prostate cancer cell lines. Compounds of the present invention are shown to be effective against prostate cancer cells and ovarian cancer cells.

BRIEF DESCRIPTION OF THE DRAWINGS

FIG. 1 illustrates one approach (scheme 1) for the synthesis of thiazolidine carboxylic acid amides. The thiazolidine carboxylic acid intermediate (2a-v) is formed upon reacting L-cysteine with various aldehydes under reported conditions (Seki et al., "A Novel Synthesis of (+)-Biotin from L-Cysteine," *J. Org. Chem.* 67:5527-5536 (2002), which is hereby incorporated by reference in its entirety). The intermediate carboxylic acid is reacted with an amine to form the corresponding amide (3-27).

In FIG. 4A, the dose and exposure time are indicated for compound 4 as follows: lane 1, 100 bp DNA marker; lane 2, 5 μM for 36 h; lane 3, 3 μM for 24 h; lane 4, 3 μM for 24 h; lane 5, 3 μM for 48 h; lane 6, 3 μM for 72 h; lane 7, 3 μM for 108 h; and lane 8, 50 μM for 36 h. In FIG. 4B, the dose and exposure time are indicated for compound 5 as follows: lane 1, 100 bp DNA marker; lane 2, 5 μM for 24 h; lane 3, 5 μM for 48 h; lane 4, 5 μM for 72 h; lane 5, 5 μM for 96 h; lane 6, 3 μM for 96 h; lane 7, 8 μM for 48 h; and lane 8, 8 μM for 72 h.

FIG. 5A shows the immunoblot results using anti-phospho AKT (S473) or anti-AKT antibodies. The immunoblots were visualized by enhanced chemiluminescence, and changes of relative levels of phospho-AKT compared to total AKT by analog treatment were quantified by densitometric analysis. FIG. 5B graphically illustrates the immunological detection of AKT using anti-AKT and anti-phospo-AKT, shown in FIG. 5A.

DETAILED DESCRIPTION OF THE INVENTION

Figure 2:
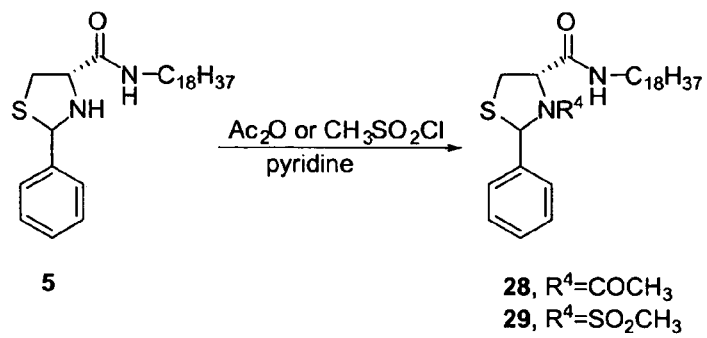
FIG. 2 illustrates one approach (scheme 2) for the synthesis of N-acyl and N-sulfonyl derivatives of the thiazolidine carboxylic acid amides. The N-acyl and N-sulfonyl derivatives (compounds 28 and 29) were synthesized from compound 5 by standard procedures.
Figure 3:
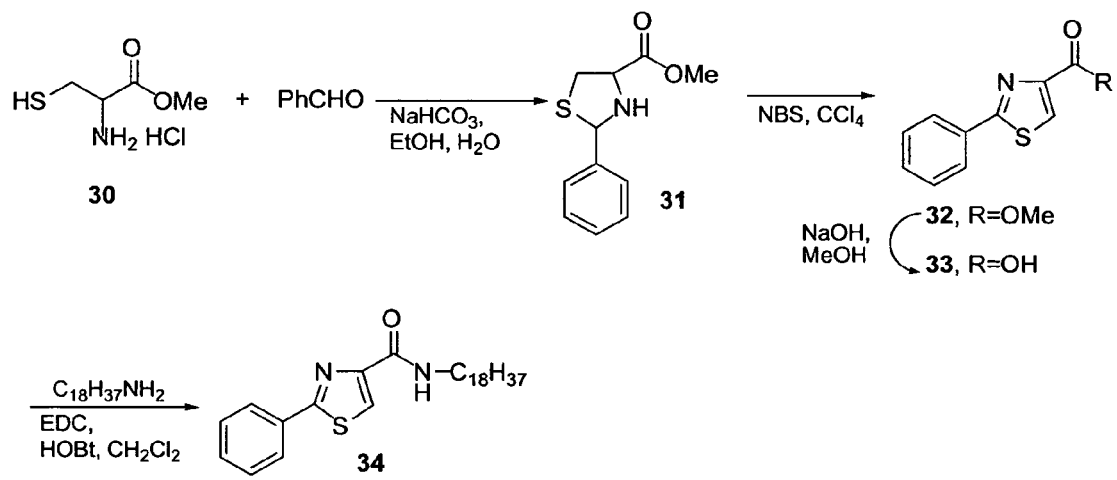
FIG. 3 illustrates one approach (scheme 3) for the synthesis of thiazole carboxylic acid amides. The thiazolidine carboxylic acid methyl ester was converted to the thiazole carboxylic acid methyl ester following a reported procedure (Badr et al., "Synthesis of Oxazolidines, Thiazolidines, and 5,6,7,8-Tetrahydro-1H, 3H-pyrrolo[1,2-c]Oxazole (or Thiazole)-1,3-diones from β-Hydroxy- or β-Mercapto-α-amino Acid Esters," *Bull. Chem. Soc. Jpn.* 54:1844-1847 (1981), which is hereby incorporated by reference in its entirety), and then converted to the alkylamide.

One aspect of the invention relates to compounds according to formulae (I) and (II) below

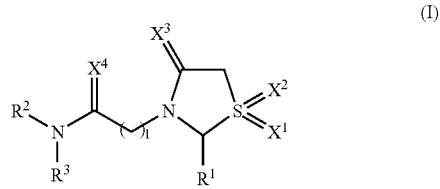

-continued

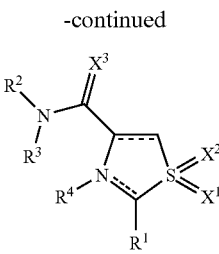
(II)

wherein
X¹ and X² are each optional, and each can be oxygen;
X³ and X⁴ are each optional, and each can be oxygen or sulfur;
l is an integer from 1 to 12;
R¹ is selected from the group of saturated or unsaturated cyclic hydrocarbons, saturated or unsaturated N-heterocycles, saturated or unsaturated O-heterocycles, saturated or unsaturated S-heterocycles, saturated or unsaturated mixed heterocycles, aliphatic or non-aliphatic straight- or branched-chain C1 to C30 hydrocarbons, or

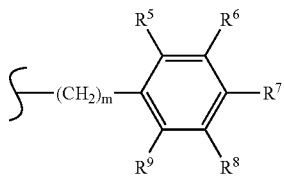

or —(CH₂)ₘ—Y¹ where m is an integer from 0 to 10 and Y¹ is a saturated or unsaturated cyclic hydrocarbon, saturated or unsaturated N-heterocycle, saturated or unsaturated O-heterocycle, saturated or unsaturated S-heterocycle, or saturated or unsaturated mixed heterocycle;
R² is hydrogen, an aliphatic or non-aliphatic straight- or branched-chain C1 to C30 hydrocarbon, R¹⁰—N(Z)-hydrocarbon- or R¹⁰-hydrocarbon- where the hydrocarbon group is an aliphatic or non-aliphatic straight- or branched-chain C1 to C30 hydrocarbon, a saturated or unsaturated cyclic hydrocarbons, a saturated or unsaturated N-heterocycle, a saturated or unsaturated O-heterocycle, a saturated or unsaturated S-heterocycle, a saturated or unsaturated mixed heterocycle, or

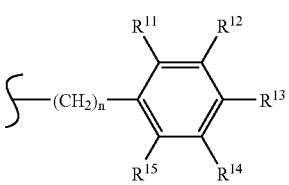

or —(CH₂)ₙ—Y² where n is an integer from 0 to 10 and Y² is a saturated or unsaturated cyclic hydrocarbon, saturated or unsaturated N-heterocycle, saturated or unsaturated O-heterocycle, saturated or unsaturated S-heterocycle, or saturated or unsaturated mixed heterocycle;
R³ is hydrogen or an aliphatic or non-aliphatic straight- or branched-chain C1 to C10 hydrocarbon;

R⁴ is optional, or can be hydrogen, an aliphatic or non-aliphatic straight- or branched-chain C1 to C10 hydrocarbon, acyl, acetyl, or mesyl;
R⁵, R⁶, R⁷, R⁸, R⁹, R¹¹, R¹², R¹³, R¹⁴, and R¹⁵ are independently selected from the group of hydrogen, hydroxyl, an aliphatic or non-aliphatic straight- or branched-chain C1 to C10 hydrocarbon, alkoxy, aryloxy, nitro, cyano, chloro, fluoro, bromo, iodo, haloalkyl, dihaloalkyl, trihaloalkyl, amino, alkylamino, dialkylamino, acylamino, arylamino, amido, alkylamido, dialkylamido, arylamido, aryl, C5 to C7 cycloalkyl, arylalkyl;
R¹⁰ is H(Z)N—, H(Z)N-hydrocarbon-, H(Z)N-hydrocarbon-N(Z)-hydrocarbon-, H(Z)N-hydrocarbon-O-hydrocarbon-, hydrocarbon hydrocarbon-, hydrocarbon-N(Z)-hydrocarbon-, H(Z)N-hydrocarbon-carbonyl-hydrocarbon-, hydrocarbon-carbonyl-hydrocarbon-, H(Z)N-phenyl-, H(Z)N-phenylalkyl-, H(Z)N-phenylalkyl-N(Z)-hydrocarbon-, H(Z)N-phenylalkyl-O-hydrocarbon-, phenylalkyl hydrocarbon-, phenylalkyl-N(Z)-hydrocarbon-, H(Z)N-phenylalkyl-carbonyl-hydrocarbon-, or phenylalkyl-carbonyl-hydrocarbon-, wherein each hydrocarbon is independently an aliphatic or non-aliphatic straight- or branched-chain C1 to C10 group, and wherein each alkyl is a C1 to C10 alkyl; and
Z is independently hydrogen or t-butoxycarbonyl.

As used herein, "aliphatic or non-aliphatic straight- or branched-chain hydrocarbon" refers to both alkylene groups that contain a single carbon and up to a defined upper limit, as well as alkenyl groups and alkynyl groups that contain two carbons up to the upper limit, whether the carbons are present in a single chain or a branched chain. Unless specifically identified, a hydrocarbon can include up to about carbons, or up to about 20 hydrocarbons, or up to about 10 hydrocarbons.

As used herein, the term "alkyl" can be any straight- or branched-chain alkyl group containing up to about 30 carbons unless otherwise specified. The alkyl group can be a sole constituent or it can be a component of a larger constituent, such as in an alkoxy, arylalkyl, alkylamino, etc.

As used herein, "saturated or unsaturated cyclic hydrocarbons" can be any such cyclic hydrocarbon, including but not limited to phenyl, biphenyl, triphenyl, naphthyl, cycloalkyl, cycloalkenyl, cyclodienyl, etc.; "saturated or unsaturated N-heterocycles" can be any such N-containing heterocycle, including but not limited to aza- and diazacycloalkyls such as aziridinyl, azetidinyl, diazatidinyl, pyrrolidinyl, piperidinyl, piperazinyl, and azocanyl, pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzimidazolyl, indazolyl, quinolizinyl, cinnolinyl, quinalolinyl, phthalazinyl, naphthyridinyl, quinoxalinyl, etc.; "saturated or unsaturated O-heterocycles" can be any such O-containing heterocycle including but not limited to oxiranyl, oxetanyl, tetrahydrofuranyl, tetrahydropyranyl, dioxanyl, furanyl, pyrylium, benzofuranyl, etc.; "saturated or unsaturated S-heterocycles" can be any such S-containing heterocycle, including but not limited to thiranyl, thietanyl, tetrahydrothiophenyl, dithiolanyl, tetrahydrothiopyranyl, thiophenyl, thiepinyl, thianaphthenyl, etc.; "saturated or unsaturated mixed heterocycles" can be any heterocycle containing two or more S-, N-, or O-heteroatoms, including but not limited to oxathiolanyl, morpholinyl, thioxanyl, thiazolyl, isothiazolyl, thiadiazolyl, oxazolyl, isoxazolyl, oxadiaziolyl, etc.

Preferred R¹ groups include benzyl, furanyl, indolyl, pyridinyl, phenyl, or substituted phenyl (with $R^5$-$R^9$ as defined above).

Preferred R² groups include aliphatic or non-aliphatic straight- or branched-chain C1 to C30 hydrocarbons, phenyl, phenylalkyls, substituted phenyls and substituted phenylalkyls with $R^{11}$-$R^{15}$ groups as defined above. Preferred aliphatic or non-aliphatic straight- or branched-chain hydrocarbons are C8 to C24 hydrocarbons, including C10 to C20 alkyls, more preferably C14 to C18 alkyls.

Preferred R³ groups include hydrogen and C1 to C10 alkyls.

Preferred R⁴ groups include hydrogen, acyl, acetyl, and mesyl.

Preferred $R^{10}$ groups are polyamines.

The integer 1 is preferably from 1 to 10, more preferably 1 to 8, 1 to 6, or 1 to 4. The integer m is preferably from 0 to 8, 0 to 6, 0 to 4, or 0 to 2. The integer n is preferably from 0 to 8, 0 to 6, 0 to 4, or 0 to 2.

Exemplary compounds according to formula (I) include, without limitation: 2-(4-oxo-2-phenylthiazolidin-3-yl)acetamide (compound 65), N-decyl-2-(4-oxo-2-phenylthiazolidin-3-yl)acetamide (compound 66), N-tetradecyl-2-(4-oxo-2-phenylthiazolidin-3-yl)acetamide (compound 67), N-octadecyl-2-(4-oxo-2-phenylthiazolidin-3-yl)acetamide (compound 68), N-octadecyl-2-(4-oxo-2-biphenylthiazolidin-3-yl)acetamide (compound 69), 2-(2-(1-(dimethylamino)naphthalen-4-yl)-4-oxothiazolidin-3-yl)-N-octadecylacetamide (compound 70), 2-(2-(4-methoxyphenyl)-4-oxothiazolidin-3-yl)-N-octadecylacetamide (compound 71), 2-(2-(2,6-dichlorophenyl)-4-oxothiazolidin-3-yl)-N-octadecylacetamide (compound 72), N-octadecyl-2-(4-oxo-2-phenyl-1-sulfoxide-thiazolidin-3-yl)acetamide (compound 80), N-octadecyl-2-(4-oxo-2-phenyl-1-sulfonyl-thiazolidin-3-yl) acetamide (compound 81), N-(3,5-difluorophenyl)-2-(4-oxo-2-phenylthiazolidin-3-yl)acetamide (compound 73), N-(3,5-difluorophenyl)-2-(4-oxo-2-phenylthiazolidin-3-yl) ethanethioamide, N-(3,5-bis(trifluoromethyl)phenyl)-2-(4-oxo-2-phenylthiazolidin-3-yl)acetamide (compound 74), N-(3,5-dichlorophenyl)-2-(4-oxo-2-phenylthiazolidin-3-yl) acetamide (compound 75), N-(2,4-dimethoxyphenyl)-2-(4-oxo-2-phenylthiazolidin-3-yl)acetamide (compound 76), N-(naphthalen-1-yl)-2-(4-oxo-2-phenylthiazolidin-3-yl)acetamide (compound 77), 3-(2-(octadecylamino)ethyl)-2-phenylthiazolidin-4-one (compound 79), N-(2-(2-phenylthiazolidin-3-yl)ethyl)octadecan-1-amine, and salts thereof.

Preferred compounds according to formula (I) include compounds 68, 71, 80, and 81.

Exemplary compounds according to formula (II) include, without limitation: (4R)-2-(4-methoxyphenyl)-N-octadecylthiazolidine-4-carboxamide (compound 15); (4R)-2-(4-ethoxyphenyl)-N-octadecylthiazolidine-4-carboxamide; N-octadecyl-2-phenylthiazole-4-carboxamide (compound 34); (4R)-2-(3,5-difluorophenyl)-N-octadecylthiazolidine-4-carboxamide (compound 23); (4R)-2-(4-cyanophenyl)-N-octadecylthiazolidine-4-carboxamide (compound 22); (4R)-N-octadecyl-N-mesyl-2-phenylthiazolidine-4-carboxamide (compound 29); (4R)-N-octadecyl-N-acetyl-2-phenylthiazolidine-4-carboxamide (compound 28); (4R)-N-heptyl-2-phenylthiazolidine-4-carboxamide (compound 3); (4R)-N-octadecyl-2-phenylthiazolidine-4-carboxamide (compound 5, R-isomer); (4S)-N-octadecyl-2-phenylthiazolidine-4-carboxamide (compound 5, S-isomer); (4R)-N-tetradecyl-2-phenylthiazolidine-4-carboxamide hydrochloride (compound 4); (4R)-N-octadecyl-2-biphenylthiazolidine-4-carboxamide (compound 27); (4R)-2-dodecyl-N-octadecylthiazolidine-4-carboxamide (compound 7); (4R)-N-octadecyl-2-(pyridin-3-yl)thiazolidine-4-carboxamide (compound 11); 2-(furan-3-yl)-N-octadecylthiazolidine-4-carboxamide (compound 12); (4R)-N-nonadecyl-2-phenylthiazolidine-4-carboxamide (compound 6); (4R)-2-(4-hydroxyphenyl)-N-octadecylthiazolidine-4-carboxamide; 2-(3-hydroxyphenyl)-N-octadecylthiazolidine-4-carboxamide (compound 14); (4R)-2-(2,4,6-trimethoxyphenyl)-N-octadecylthiazolidine-4-carboxamide; 2-(3,4-dimethoxyphenyl)-N-octadecylthiazolidine-4-carboxamide (compound 16); 2-(3,4,5-trimethoxyphenyl)-N-octadecylthiazolidine-4-carboxamide (compound 17); 2-(4-acetamidophenyl)-N-octadecylthiazolidine-4-carboxamide (compound 18); (4R)-2-(4-fluorophenyl)-N-octadecylthiazolidine-4-carboxamide (compound 19); (4R)-2-(2,6-dichlorophenyl)-N-octadecylthiazolidine-4-carboxamide (compound 24); (4R)-2-(4-bromophenyl)-N-octadecylthiazolidine-4-carboxamide (compound 20); (4R)-N-octadecyl-2-p-tolylthiazolidine-4-carboxamide (compound 26); (4R)-2-cyclohexyl-N-octadecylthiazolidine-4-carboxamide (compound 8); 2-(4-nitrophenyl)-N-octadecylthiazolidine-4-carboxamide (compound 21); (4R)-2-(4-(dimethylamino)phenyl)-N-octadecylthiazolidine-4-carboxamide (compound 13); (4R)-2-(1H-indol-3-yl)-N-octadecylthiazolidine-4-carboxamide (compound 10); (4R)-2-benzyl-N-octadecylthiazolidine-4-carboxamide (compound 9); (4R)-2-(3-bromo-4-fluorophenyl)-N-octadecylthiazolidine-4-carboxamide (compound 25); (4R)-2-(3,4,5-trimethoxyphenyl)-N,N-dioctylthiazolidine-4-carboxamide; and salts thereof.

Preferred compounds according to formula (II) include compounds 5 (R-isomer), 13, 14, 16, 17, 18, 19, 25, and 26.

The compounds of the present invention and their intermediates can be synthesized using commercially available or readily synthesized reactants.

Figure 6:
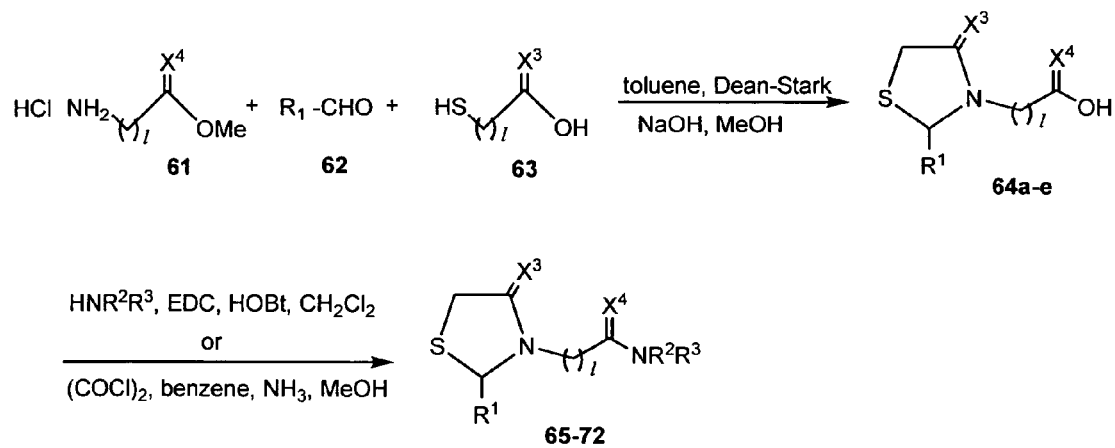
FIG. 6 illustrates one approach (scheme 4) for the synthesis of 4-thiazolidinone carboxylic acids, and their conversion to corresponding amides by reaction with primary or secondary amines (HNR²R³). As shown in this reaction scheme, different starting materials (where 1 differs) can be used to prepare various compounds of the invention.

By way of example, the compounds according to formula (I) can be synthesized according to scheme 4 illustrated in FIG. 6. According to one approach, an intermediate acid according to formula (III)

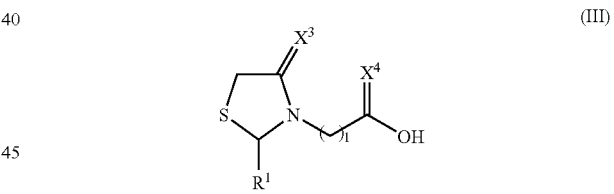

Figure 7:
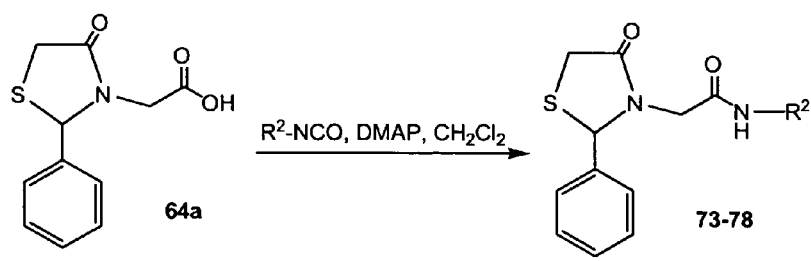
FIG. 7 illustrates a second approach (scheme 5) for the synthesis of 4-thiazolidinone carboxylic acids, and their conversion to corresponding amides by reaction with R²—CNO.

(where l, R¹, X³, and X⁴ are as defined above) is reacted with appropriate amines in the presence of EDC/HOBt under standard conditions. The intermediate acids can be prepared initially via condensing mercaptoacetic acid, glycine methyl ester, and aromatic aldehydes in a one-pot reaction, followed by basic hydrolysis of the ester (Holmes et al., "Strategies for Combinatorial Organic Synthesis: Solution and Polymer-Supported Synthesis of 4-Thiazolidinones and 4-Metathiazanones Derived from Amino Acids," *J. Org. Chem.* 60:7328-7333 (1995), which is hereby incorporated by reference in its entirety). By substituting glycine methyl ester with analogs containing longer carbon backbones, it becomes possible to prepare compounds according to formula (III) and, ultimately, formula (I), with l being greater than 1 (i.e., containing an alkylene group that is longer than methylene). According to a second approach, the thiazolidinone amides of formula (I) can also be prepared by a simple and direct method (Schuemacher et al., "Condensation Between Isocyanates and Carboxylic Acids in the Presence of 4-Dimethylaminopyridine (DMAP), a Mild and Efficient Synthesis of Amides," *Synthesis* 22:243-246 (2001), which is hereby incorporated by reference in its entirety), which involves reaction of the intermediate acid with desired isocyanates in the presence of a catalytic amount of DMAP (FIG. 7) (scheme 5).

Figure 8:
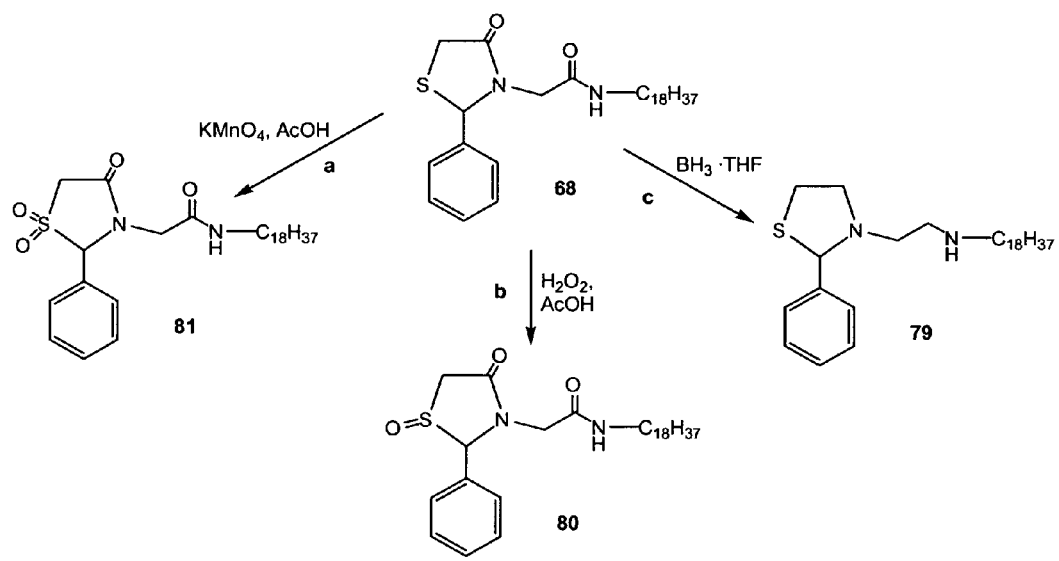
FIG. 8 illustrates three approaches for modifying the core structure of the thiazolidinone compounds of the present invention (scheme 6) to afford ring-bound sulfone or sulfoxide groups (steps a and b, respectively), as well as the complete reduction of carbonyl groups (step c).

Further modification of the thiazolidinone compounds can be achieved by, e.g., exhaustive reduction of using $BH_3 \cdot THF$ under reflux conditions to eliminate carbonyl or sulfoxide groups $X^3$ and $X^4$ (FIG. 8) (scheme 6c), as well as oxidation of a compound using $H_2O_2$ and $KMnO_4$ to afford sulfoxides or sulfones, respectively, as shown in scheme 6a and 6b.

Also by way of example, compounds according to formula (II) can be prepared by reacting an intermediate acid according to formula (IV),

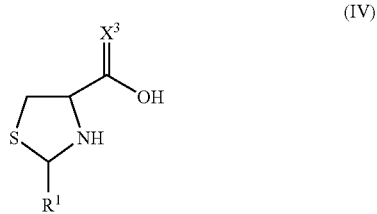

(IV)

where compound (IV) can be either the R- or S-stereoisomer and $R^1$ and $X^3$ are defined as above, with appropriate amines in the presence of EDC/HOBt under standard conditions. The intermediate acids can be prepared via reaction of L-cysteine with desired aldehydes under reported conditions (Seki et al., "A Novel Synthesis of (+)-Biotin from L-Cysteine," *J. Org. Chem.* 67:5527-5536 (2002), which is hereby incorporated by reference in its entirety).

The compounds of the present invention can also be modified to contain a polymeric conjugate. Suitable polymeric conjugates include, without limitation, poly(alkyl) amines, poly(alkoxy)amine, polyamines, etc. It is also well known that polyamine containing compounds exhibit a number of biological activities and have been utilized as chemotherapeutic agents. Exemplary conjugates include those containing the naturally occurring polyamines like putrescine, spermidine, and spermine, as well as synthetic polyamines.

Figure 9:
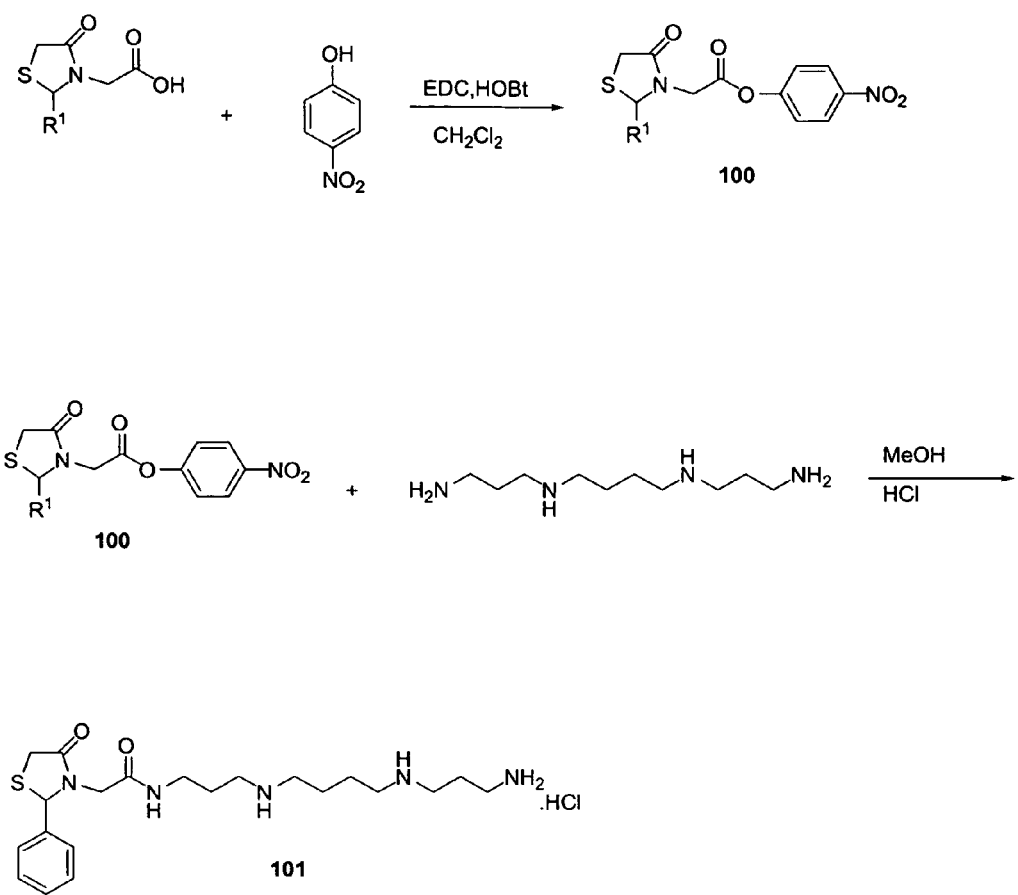
FIG. 9 illustrates a process for the synthesis of polyamine conjugates of thiazolidinone amides.

According to one approach, a compound of the present invention can be conjugated to a polyamine by reacting the intermediate acid or a nitrophenyl derivative thereof with a polyamine $NH_2$—$R^2$ where $R^2$ is $R^{10}$—N(Z)-hydrocarbon- or $R^{10}$-hydrocarbon-, with $R^{10}$ and Z being as defined above. An exemplary synthesis scheme is illustrated in FIG. 9.

The compounds can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

The compounds of the present invention can be present in the form of a racemic mixture, containing substantially equivalent amounts of stereoisomers. In another embodiment, the compounds of the present invention can be prepared or otherwise isolated, using known procedures, to obtain a stereoisomer substantially free of its corresponding stereoisomer (i.e., substantially pure). By substantially pure, it is intended that a stereoisomer is at least about 95% pure, more preferably at least about 98% pure, most preferably at least about 99% pure.

Another aspect of the present invention relates to pharmaceutical compositions that contain one or more of the above-identified compounds of the present invention. Typically, the pharmaceutical composition of the present invention will include a compound of the present invention or its pharmaceutically acceptable salt, as well as a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients. For example, application to mucous membranes can be achieved with an aerosol spray containing small particles of a compound of this invention in a spray or dry powder form.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

For oral therapeutic administration, these active compounds can be incorporated with excipients and used in the form of tablets, capsules, elixirs, suspensions, syrups, and the like. Such compositions and preparations should contain at least 0.1% of active compound. The percentage of the compound in these compositions can, of course, be varied and can conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 mg and 800 mg of active compound.

The active compounds of the present invention may be orally administered, for example, with an inert diluent, or with an assimilable edible carrier, or they can be enclosed in hard or soft shell capsules, or they can be compressed into tablets, or they can be incorporated directly with the food of the diet.

The pharmaceutical forms suitable for injectable use include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds or pharmaceutical compositions of the present invention may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The compounds of the present invention are particularly useful in the treatment or prevention of various forms of cancer, particularly prostate cancer, breast cancer, and ovarian cancer. It is believed that other forms of cancer will likewise be treatable or preventable upon administration of the compounds or compositions of the present invention to a patient. Preferred compounds of the present invention are selectively disruptive to cancer cells, causing ablation of cancer cells but not normal cells. Significantly, harm to normal cells is minimized because the cancer cells are susceptible to disruption at much lower concentrations of the compounds of the present invention.

Thus, a further aspect of the present invention relates to a method of destroying a cancerous cell that includes: providing a compound of the present invention and then contacting a cancerous cell with the compound under conditions effective to destroy the contacted cancerous cell. According to various embodiments of destroying the cancerous cells, the cells to be destroyed can be located either in vivo or ex vivo (i.e., in culture).

A still further aspect of the present invention relates to a method of treating or preventing a cancerous condition that includes: providing a compound of the present invention and then administering an effective amount of the compound to a patient in a manner effective to treat or prevent a cancerous condition.

According to one embodiment, the patient to be treated is characterized by the presence of a precancerous condition, and the administering of the compound is effective to prevent development of the precancerous condition into the cancerous condition. This can occur by destroying the precancerous cell prior to or concurrent with its further development into a cancerous state.

According to another embodiment, the patient to be treated is characterized by the presence of a cancerous condition, and the administering of the compound is effective either to cause regression of the cancerous condition or to inhibit growth of the cancerous condition. This preferably occurs by destroying cancer cells, regardless of their location in the patient body. That is, whether the cancer cells are located at a primary tumor site or whether the cancer cells have metastasized and created secondary tumors within the patient body.

As used herein, patient refers to any mammalian patient, including without limitation, humans and other primates, dogs, cats, horses, cows, sheep, pigs, rats, mice, and other rodents.

When administering the compounds of the present invention, they can be administered systemically or, alternatively, they can be administered directly to a specific site where cancer cells or precancerous cells are present. Thus, administering can be accomplished in any manner effective for delivering the compounds or the pharmaceutical compositions to the cancer cells or precancerous cells. Exemplary modes of administration include, without limitation, administering the compounds or compositions orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

When the compounds or pharmaceutical compositions of the present invention are administered to treat or prevent a cancerous condition, the pharmaceutical composition can also contain, or can be administered in conjunction with, other therapeutic agents or treatment regimen presently known or hereafter developed for the treatment of various types of cancer. Examples of other therapeutic agents or treatment regimen include, without limitation, radiation therapy, chemotherapy, surgical intervention, and combinations thereof.

Compositions within the scope of this invention include all compositions wherein the compound of the present invention is contained in an amount effective to achieve its intended purpose. While individual needs may vary, determination of optimal ranges of effective amounts of each component is within the skill of the art. Typical dosages comprise about 0.01 to about 100 mg/kg·body wt. The preferred dosages comprise about 0.1 to about 100 mg/kg·body wt. The most preferred dosages comprise about 4.47 (t, J=7.2 Hz, 0.4H), 3.55-3.71 (m, 1H), 3.25-3.35 (m, 1H), 3.10-3.16 (m, 2H), 1.44 (m, 2H), 1.23 (s, 22H), 0.85 (t, J=6.3 Hz, 3H); MS (ESI) m/z calcd for $C_{24}H_{40}N_2OS$: 404.65; (M$^+$), obsd 427.30 (M+Na).

(2RS, 4R)-2-Phenylthiazolidine-4-carboxylic acid octadecylamide Hydrochloride (compound 5.HCl): $^1$H NMR (DMSO-d$_6$) δ 8.59 (d, J=5.1 Hz, 1H), 7.63 (d, J=3.9 Hz, 2H), 7.42-7.47 (m, 3H), 5.86 (s, 0.6H), 5.81(s, 0.4H), 4.60 (t, J=6.3 Hz, 0.6H), 4.39 (t, J=6.9 Hz, 0.4H), 3.52-3.66 (m, 1H), 3.24-3.30 (m, 1H), 3.10-3.16 (m, 2H), 1.42 (m, 2H), 1.23 (s, 30H), 0.85 (t, J=6.3 Hz, 3H); MS (ESI) m/z calcd for $C_{28}H_{49}N_2OS$: 461.76; (M+1), obsd 461.50.

(2RS, 4R)-2-Phenylthiazolidine-4-carboxylic acid nonadecylamide Hydrochloride (compound 6.HCl): $^1$H NMR (DMSO-d$_6$) δ 8.51 (s, 1H), 7.62 (m, 2H), 7.41-7.46 (m, 3H), 5.83 (s, 0.6H), 5.78 (s, 0.4H), 4.53 (m, 0.6H), 4.32 (m, 0.4H), 3.48-3.61 (m, 1H), 3.24-3.29 (m, 1H), 3.11-3.15 (m, 2H), 1.43 (m, 2H), 1.23 (s, 32H), 0.85 (t, J=6.3 Hz, 3H); MS (ESI) m/z calcd for $C_{29}H_{50}N_2OS$: 474.79; (M$^+$), obsd 497.40 (M+Na).

(2RS, 4R)-2-Dodecylthiazolidine-4-carboxylic acid octadecylamide (compound 7): $^1$H NMR (CDCl$_3$) δ 7.18 (m, 1H), 4.20-4.27 (m, 1H), 3.79 (m, 0.3H), 3.54-3.59 (m, 0.7H), 3.08-3.34 (m, 4H), 1.65-1.78 (m, 2H), 1.43-1.51 (m, 4H), 1.27 (brs, 48H), 0.89 (t, J=6 Hz, 6H); MS (ESI) m/z calcd for $C_{34}H_{69}N_2OS$: 553.98; (M+1), obsd 553.60.

(2RS, 4R)-2-Cyclohexylthiazolidine-4-carboxylic acid octadecylamide (compound 8): $^1$H NMR (CDCl$_3$) δ 7.17 (m, 1H), 4.10-4.20 (m, 1H), 3.76 (m, 0.3H), 3.54 (dd, J=11.1, 3.6 Hz, 0.7H), 2.97-3.34 (m, 4H), 2.02 (m, 1H), 1.68-1.78 (m, 4H), 1.48-1.54 (m, 2H), 1.27 (brs, 36H), 0.87 (t, J=6.9 Hz, 3H); MS (ESI) m/z calcd for $C_{28}H_{55}N_2OS$: 467.81; (M+1), obsd 467.60.

(2RS, 4R)-2-Benzylthiazolidine-4-carboxylic acid octadecylamide (compound 9): $^1$H NMR (CDCl$_3$) δ 7.28-7.33 (m, 5H), 7.03 (s, 0.7H), 6.48 (s, 0.3H), 4.55 (brs, 0.5H), 4.18 (brs, 0.5H), 3.82 (brs, 0.3H), 3.54 (dd, J=11.1, 3.6 Hz, 0.7H), 2.99-3.31 (m, 6H), 1.46-1.51 (m, 2H), 1.27 (brs, 30H), 0.89 (t, J=6.3 Hz, 3H); MS (ESI) m/z calcd for $C_{29}H_{50}N_2OS$: 475.79; (M+1), obsd 475.50.

(2RS, 4R)-2-(1H-Indol-3yl)-thiazolidine-4-carboxylic acid octadecylamide (compound 10): $^1$H NMR (CDCl$_3$) δ 7.86 (m, 0.6H), 7.77 (m, 0.4H), 7.41-7.48 (m, 4H), 7.29-7.34 (m, 1H), 6.0 (s, 0.3H), 5.69 (s, 0.7H), 4.37-4.41 (m, 0.5H), 3.76 (dd, J=11.1, 4.2 Hz, 0.5H), 3.23-3.52 (m, 3H), 2.79-3.04 (m, 1H), 1.43 (m, 2H), 1.27 (s, 30H), 0.89 (t, J=6.6 Hz, 3H); MS (ESI) m/z calcd for $C_{30}H_{50}N_3OS$: 500.80; (M+1), obsd 500.60.

(2RS, 4R)-2-Pyridin-3-yl-thiazolidine-4-carboxylic acid octadecylamide (compound 11): $^1$H NMR (CDCl$_3$) δ 8.74 (d, J=2.1 Hz, 1H), 8.60 (d, J=4.8 Hz, 1H), 7.84 (d, J=7.8 Hz, 1H), 7.31-7.36 (m, 1H), 7.08 (m, 1H), 5.44 (s, 0.5H), 5.40 (s, 0.5H), 4.28-4.35 (m, 1H), 3.72 (dd, J=11.1, 4.2 Hz, 1H), 3.27-3.45 (m, 3H), 2.57 (m, 1H), 1.53-1.57 (m, 2H), 1.26 (s, 30H), 0.89 (t, J=6.6 Hz, 3H); MS (ESI) m/z calcd for $C_{27}H_{49}N_3OS$: 462.75; (M+1), obsd 462.40.

(2RS, 4R)-2-Furan-3-yl-thiazolidine-4-carboxylic acid Hydrochloride (compound 12.HCl): $^1$H NMR (DMSO-d$_6$) δ 8.59 (d, J=15.6 Hz, 1H), 7.89 (d, J=8.1 Hz, 1H), 7.72 (s, 1H), 5.86 (s, 0.7H), 5.78 (s, 0.3H), 4.37-4.56 (m, 1H), 3.50-3.63 (m, 1H), 3.11-3.23 (m, 3H), 1.43 (m, 2H), 1.23 (s, 30H), 0.85 (t, J=6.6 Hz, 3H); MS (ESI) m/z calcd for $C_{26}H_{48}N_2O_2S$: 451.72; (M+1), obsd 451.60.

(2RS, 4R)-2-(4-Dimethylamino-phenyl)-thiazolidine-4-carboxylic acid octadecylamide (compound 13): $^1$H NMR (CDCl$_3$) δ 7.34-7.41 (m, 2H), 6.70-6.74 (m, 2H), 5.57 (s, 0.3H), 5.28 (s, 0.7H), 4.34 (m, 0.7H), 3.90 (m, 0.3H), 3.69

(dd, J=11.1, 4.2 Hz, 1H), 3.41-3.47 (m, 1H), 3.20-3.33 (m, 2H), 2.97 (d, J=3.6 Hz, 6H), 1.48-1.55 (m, 2H), 1.27 (s, 30H), 0.89 (t, J=6.3 Hz, 3H); MS (ESI) m/z calcd for $C_{30}H_{54}N_3OS$: 504.83; (M+1), obsd 504.60.

(2RS, 4R)-2-(3-Hydroxy-phenyl)-thiazolidine-4-carboxylic acid octadecylamide (compound 14): $^1$H NMR (DMSO-$d_6$) δ 8.59 (s, 1H), 7.22 (t, J=6.6 Hz, 1H), 7.02 (d, J=6.3 Hz, 2H), 6.82 (d, J=7.5 Hz, 1H), 5.77 (s, 0.7H), 5.71 (s, 0.3H), 4.545 (m, 0.7H), 4.37 (m, 0.3H), 3.49-3.59 (m, 1H), 3.13-3.27 (m, 3H), 1.43 (brs, 2H), 1.23 (s, 30H), 0.85 (t, J=6.3 Hz, 3H); MS (ESI) m/z calcd for $C_{28}H_{49}N_2O_2S$: 477.76; (M+1), obsd 477.60.

(2RS, 4R)-2-(4-Methoxy-phenyl)-thiazolidine-4-carboxylic acid octadecylamide Hydrochloride (compound 15.HCl): $^1$H NMR (DMSO-$d_6$) δ 8.61 (m, 1H), 7.57 (d, J=8.4 Hz, 2H), 6.98 (d, J=9 Hz, 2H), 5.83 (s, 0.7H), 5.78 (s, 0.3H), 4.61 (t, J=6.3 Hz, 0.7H), 4.40 (m, 0.3H), 3.77 (s, 3H), 3.51-3.70 (m, 1H), 3.22-3.31 (m, 1H), 3.11 (m, 2H), 1.43 (m, 2H), 1.23 (s, 30H), 0.84 (t, J=6.6 Hz, 3H); MS (ESI) m/z calcd for $C_{29}H_{51}N_2O_2S$: 491.79; (M+1), obsd 491.60.

(2RS, 4R)-2-(3,4-Dimethoxy-phenyl)-thiazolidine-4-carboxylic acid octadecylamide Hydrochloride (compound 16.HCl): $^1$H NMR (DMSO-$d_6$) δ 8.58 (m, 1H), 7.33 (d, J=4.2 Hz, 1H), 7.14 (t, J=7.5 Hz, 1H), 6.97 (d, J=8.4 Hz, 1H), 5.81 (s, 0.8H), 5.77 (s, 0.2H), 4.62 (m, 0.7H), 4.40 (m, 0.3H), 3.78 (d, J=7.8 Hz, 6H), 3.52-3.68 (m, 1H), 3.23-3.29 (m, 1H), 3.12-3.13 (m, 2H), 1.43 (m, 2H), 1.23 (s, 30H), 0.85 (t, J=6.6 Hz, 3H); MS (ESI) m/z calcd for $C_{30}H_{53}N_2O_3S$: 521.81; (M+1), obsd 521.60.

(2RS, 4R)-2-(3,4,5-Trimethoxy-phenyl)-thiazolidine-4-carboxylic acid octadecylamide Hydrochloride (compound 17.HCl): $^1$H NMR (DMSO-$d_6$) δ 8.59 (m, 1H), 7.01 (d, J=5.7 Hz, 2H), 5.80 (s, 0.8H), 5.76 (s, 0.2H), 4.63 (m, 0.7H), 4.73 (m, 0.3H), 3.80 (d, J=5.7 Hz, 6H), 3.66 (s, 3H), 3.23-3.28 (m, 1H), 3.12-3.13 (m, 2H), 1.43 (m, 2H), 1.23 (s, 30H), 0.85 (t, J=6 Hz, 3H); MS (ESI) m/z calcd for $C_{31}H_{55}N_2O_4S$: 551.84; (M+1), obsd 551.60.

(2RS, 4R)-2-(4-Acetylamino-phenyl)-thiazolidine-4-carboxylic acid octadecylamide Hydrochloride (compound 18.HCl): $^1$H NMR (DMSO-$d_6$) δ 10.18 (s, 1H), 8.61 (m, 1H), 7.54-7.64 (m, 4H), 5.82 (s, 0.7H), 5.77 (s, 0.3H), 4.60 (m, 0.8H), 4.42 (m, 0.2H), 3.56-3.64 (m, 1H), 3.12-3.26 (m, 3H), 2.05 (s, 3H), 1.43 (m, 2H), 1.23 (s, 30H), 0.84 (t, J=6 Hz, 3H); MS (ESI) m/z calcd for $C_{30}H_{52}N_3O_2S$: 518.81; (M+1), obsd 518.70.

(2RS, 4R)-2-(4-Fluoro-phenyl)-thiazolidine-4-carboxylic acid octadecylamide (compound 19): $^1$H NMR (CDCl$_3$) δ 7.46-7.54 (m, 2H), 7.13-7.20 (m, 1H), 7.01-7.08 (m, 2H), 5.60 (s, 0.3H), 5.34 (s, 0.7H), 4.76 (m, 0.3H), 4.34 (m, 0.7H), 3.69 (dd, J=11.1, 6.9 Hz, 1H), 3.21-3.52 (m, 3H), 1.49 (m, 2H), 1.26 (s, 30H), 0.89 (t, J=6.3 Hz, 3H); MS (ESI) m/z calcd for $C_{28}H_{48}FN_2OS$: 479.75; (M+1), obsd 479.60.

(2RS, 4R)-2-(4-Bromo-phenyl)-thiazolidine-4-carboxylic acid octadecylamide (compound 20): $^1$H NMR (CDCl$_3$) δ 7.48-7.62 (m, 2H), 7.36-7.42 (m, 2H), 7.14 (m, 0.7H), 6.40 (m, 0.3), 5.57 (d,J=10.2 Hz, 0.3H), 5.33 (d, J=11.1 Hz, 0.7H), 4.32 (m, 0.7H), 3.94 (m, 0.3H), 3.70 (dd, J=11.1, 4.2 Hz, 1H), 3.20-3.44 (m, 3H), 1.49 (m, 2H), 1.27 (s, 30H), 0.89 (t, J=6.3 Hz, 3H); MS (ESI) m/z calcd for $C_{28}H_{47}BrN_2OS$: 539.66; (M+), obsd 539.70.

(2RS, 4R)-2-(4-Nitro-phenyl)-thiazolidine-4-carboxylic acid octadecylamide (compound 21): $^1$H NMR (CDCl$_3$) δ 8.24 (d, J=8.7 Hz, 2H), 7.67 (d, J=8.7 Hz, 2H), 6.92 (m, 1H), 5.54 (s, 0.5H), 5.50 (s, 0.5H), 4.24-4.31 (m, 1H), 3.67 (dd, J=10.8, 4.8 Hz, 1H), 3.27-3.44 (m, 1H), 1.55 (m, 2H), 1.26 (s, 30H), 0.89 (t, J=6.3 Hz, 3H); MS (ESI) m/z calcd for $C_{28}H_{47}N_3O_3S$: 506.76; (M+1), obsd 506.60.

(2RS, 4R)-2-(4-Cyano-phenyl)-thiazolidine-4-carboxylic acid octadecylamide (compound 22): $^1$H NMR (CDCl$_3$) δ 7.60-7.70 (m, 4H), 6.94 (m, 0.6H), 6.37 (m, 0.4), 5.64 (s, 0.4H), 5.46 (s, 0.6H), 4.27 (m, 0.6H), 3.96 (m, 0.4H), 3.65-3.70 (m, 1H), 3.20-3.45 (m, 3H), 1.54 (m, 2H), 1.26 (s, 30H), 0.89 (t, J=6.3 Hz, 3H); MS (ESI) m/z calcd for $C_{29}H_{47}N_3OS$: 485.77; (M+), obsd 508.50 (M+Na).

(2RS, 4R)-2-(3,5-Difluoro-phenyl)-thiazolidine-4-carboxylic acid octadecylamide (compound 23): $^1$H NMR (CDCl$_3$) δ 7.04-7.08 (m, 2H), 6.97 (m, 1H), 6.79 (m, 1H), 5.40 (s, 0.5H), 5.36 (s, 0.5H), 4.23-4.30 (m, 1H), 3.66 (dd, J=11.1, 4.5 Hz, 1H), 3.26-3.42 (m, 3H), 1.33 (m, 2H), 1.26 (s, 30H), 0.89 (t, J=6.3 Hz, 3H); MS (ESI) m/z calcd for $C_{28}H_{47}F_2N_2O_2S$: 497.74; (M+1), obsd 497.50.

(2RS, 4R)-2-(2,6-Dichloro-phenyl)-thiazolidine-4-carboxylic acid octadecylamide (compound 24): $^1$H NMR (CDCl$_3$) δ 7.34-7.38 (m, 2H), 7.15-7.28 (m, 2H), 6.29 (s, 0.5H), 6.25 (s, 0.5H), 4.25 (t, J=5.7 Hz, 1H), 3.94 (dd, J=10.5, 1.8 Hz, 1H), 3.26-3.52 (m, 3H), 1.52 (m, 2H), 1.26 (s, 30H), 0.89 (t, J=6 Hz, 3H); MS (ESI) m/z calcd for $C_{28}H_{46}Cl_2N_2O_2S$: 529.65; (M+), obsd 529.70.

(2RS, 4R)-2-(3-Bromo-4-fluoro-phenyl)-thiazolidine-4-carboxylic acid octadecylamide (compound 25): $^1$H NMR (CDCl$_3$) δ 7.71 (m, 1H), 7.42 (m, 1H), 7.06-7.16 (m, 2H), 5.56 (d, J=9.3 Hz, 0.2H), 5.34 (d, J=10.2 Hz, 0.8H), 4.29 (d, J=4.5 Hz, 0.8H), 3.94 (m, 0.2H), 3.69 (dd, J=11.1, 4.2 Hz, 1H), 3.21-3.41 (m, 3H), 1.52 (m, 2H), 1.26 (s, 30H), 0.89 (t, J=6.3 Hz, 3H); MS (ESI) m/z calcd for $C_{28}H_{47}BrFN_2OS$: 558.65; (M+1), obsd 558.70.

(2RS, 4R)-2-p-Tolyl-thiazolidine-4-carboxylic acid octadecylamide (compound 26): $^1$H NMR (CDCl$_3$) δ 7.34-7.43 (m, 2H), 7.14-7.21 (m, 3H), 5.59 (s, 0.2H), 5.32 (s, 0.8H), 4.76 (m, 0.2H), 4.35 (m, 0.8H), 3.70 (dd, J=11.1, 3.9 Hz, 1H), 3.21-3.43 (m, 3H), 2.36 (d, J=2.7 Hz, 3H), 1.51 (m, 2H), 1.27 (s, 30H), 0.89 (t, J=6.3 Hz, 3H); MS (ESI) m/z calcd for $C_{29}H_{51}N_2OS$: 475.79; (M+1), obsd 475.60.

(2RS, 4R)-2-Biphenyl-4-yl-thiazolidine-4-carboxylic acid octadecylamide Hydrochloride (compound 27-HCl): $^1$H NMR (DMSO-$d_6$) δ 8.59 (m, 1H), 7.66-7.73 (m, 5H), 7.37-7.51 (m, 4H), 5.92 (s, 0.7H), 5.87 (s, 0.3H), 4.62 (m, 0.7H), 4.41 (m, 0.3H), 3.53-3.64 (m, 1H), 3.26-3.32 (m, 1H), 3.13-3.17 (m, 2H), 1.44 (m, 2H), 1.22 (s, 30H), 0.84 (t, J=6.3 Hz, 3H); MS (ESI) m/z calcd for $C_{34}H_{53}N_2OS$: 537.86; (M+1), obsd 537.70.

Example 2

Synthesis of N-Acyl and N-sulfonyl Derivatives Thiazolidine Carboxylic Acid Amides N-Acyl and N-sulfonyl derivatives (compounds 28 and 29) were synthesized from compound 5 by standard procedures (scheme 2). Briefly, (2RS, 4R)-2-phenylthiazolidine-4-carboxylic acid octadecylamide (compound 5) was reacted with either acetic anhydride or methyl sulfonyl chloride, in pyridine, to afford the desired derivatives.

(2RS, 4R)-3-Acetyl-2-phenylthiazolidine-4-carboxylic acid octadecylamide (compound 28): $^1$H NMR (CDCl$_3$) δ 7.31-7.41 (m, 5H), 6.01 (s, 1H), 5.12 (s, 1H), 3.73 (m, 1H), 3.40 (m, 1H), 3.31 (m, 1H), 3.11-3.17 (m, 1H), 2.00 (s, 3H), 1.27-1.33 (m, 32H), 0.89 (t, J=6.3 Hz, 3H); MS (ESI) m/z calcd for $C_{30}H_{50}N_2O_2S$: 502.80; (M+), obsd 502.60.

(2RS, 4R)-3-Methanesulfonyl-2-phenylthiazolidine-4-carboxylic acid octadecylamide (compound 29): $^1$H NMR (CDCl$_3$) δ 7.65-7.68 (m, 2H), 7.32-7.36 (m, 3H), 6.20 (s, 1H), 4.63 (dd, J=9, 6 Hz, 1H), 3.67 (dd, J=12, 6 Hz, 1H), 3.47 (dd, J=12.3, 8.1 Hz, 1H), 3.04-3.13 (m, 2H), 3.02 (s, 3H), 1.27 (m, 32H), 0.89 (t, J=6.3 Hz, 3H); MS (ESI) m/z calcd for $C_{29}H_{50}N_2O_3S_2$ : 538.85; (M+), obsd 538.70.

Based on the foregoing synthesis, it is expected that other acyl anhydrides (e.g., containing larger alkyl groups) and other sulfonyl chlorides (e.g., containing larger alkyl groups) can also be prepared according to this same synthesis procedure (Badr et al., "Synthesis of Oxazolidines, Thiazolidines, and 5,6,7,8-Tetrahydro-1H, 3H-pyrrolo[1,2-c]oxazole (or thiazole)-1,3-diones from β-Hydroxy- or β-Mercapto-α-amino Acid Esters," *Bull. Chem. Soc. Jpn.* 54:1844-1847 (1981), which is hereby incorporated by reference in its entirety).

Example 3

Synthesis of Thiazole Carboxylic Acid Amides

The synthesis of thiazole derivative (compound 34) was accomplished starting from cysteine as shown in scheme 3.

To a solution of DL-cysteine (3 g, 24.76 mmol) in MeOH (50 mL) at 0° C., $SOCl_2$ (2.76 mL, 37.14 mmol) was slowly added and warmed to room temperature then refluxed for 3 h. The reaction mixture was concentrated in vacuo to yield a residue. This residue was taken in to aqueous EtOH (1:1, 30 mL), $NaHCO_3$ (2.28 g, 27.23 mmol) was added, after 10 min benzaldehyde (2.5 mL, 24.76 mmol) was added and stirring continued for 3 h. $CHCl_3$ (200 mL) was added to the reaction mixture and washed with water, brine, dried ($Na_2SO_4$) and solvent was removed in vacuo. The crude product was purified by column chromatography to afford 2-phenylthiazolidine-4-carboxylic acid methyl ester (compound 31): yield 4.7 g, 85%; $^1$H NMR (CDCl$_3$) δ 7.51-7.62 (m, 2H), 7.32-7.42 (m, 3H), 5.84 (s, 0.4H), 5.58 (s, 0.6H), 4.24 (t, J=6.3 Hz, 0.4H), 4.01 (t, J=7.5 Hz, 0.6H), 3.83 (s, 3H), 3.39-3.55 (m, 1H), 3.10-3.26 (m, 1H); MS (ESI) m/z 224; (M+1).

Beginning with compound 31, 2-phenylthiazole-4-carboxylic acid methyl ester (compound 32) was synthesized following a reported procedure (Kue et al., "Essential Role for G Proteins in Prostate Cancer Cell Growth and Signaling," *J. Urol.* 164:2162-2167 (2000), which is hereby incorporated by reference in its entirety). Yield 0.33 g, 68%; $^1$H NMR (CDCl$_3$) δ 8.20 (s, 1H), 8.0-8.04 (m, 2H), 7.45-7.50 (m, 3H), 4.0 (s, 3H); MS (ESI) m/z 220; (M+1).

To a solution of compound 32 (0.5 g, 2.28 mmol) in MeOH (10 mL) at 0° C., 1N NaOH (5 mL) was added and stirred for 2 h. To the reaction mixture EtOAc (30 mL) was added and acidified with 1N HCl. Extracted with EtOAc (3×50 mL), combined extracts were washed with water, brine, dried ($Na_2SO_4$) and solvent was removed under vacuo to give crude acid (compound 33), which was converted to 2-phenylthiazole-4-carboxylic acid octadecylamide (compound 34) following the general procedure described in Example 1 above. Yield 0.30 g, 68%; $^1$H NMR (CDCl$_3$) δ 8.10 (s, 1H), 7.96-7.93 (m, 2H), 7.46-7.50 (m, 3H), 3.49 (dd, J=13.5, 6.9 Hz, 2H), 1.69 (m, 2H), 1.27 (m, 30H), 0.89 (t, J=6.3 Hz, 3H); MS (ESI) m/z calcd for $C_{28}H_{45}N_2OS$: 457.73; (M+1), obsd 457.60.

TABLE 1

Structures and Physical Data of Synthesized Compounds

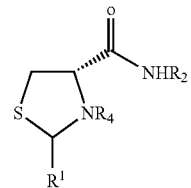

| compound | R$^1$ | R$^2$ | R$^4$ | mp (° C.) | yield (%) | formula |
|---|---|---|---|---|---|---|
| 3-HCl | phenyl | C$_7$H$_{15}$ | H | ND | 80 | C$_{17}$H$_{27}$ClN$_2$OS |
| 4-HCl | phenyl | C$_{14}$H$_{29}$ | H | 95 | 83 | C$_{24}$H$_{41}$ClN$_2$OS |
| 5-HCl | phenyl | C$_{18}$H$_{37}$ | H | 93 | 70 | C$_{28}$H$_{49}$ClN$_2$OS |
| 6-HCl | phenyl | C$_{19}$H$_{39}$ | H | 85 | 78 | C$_{29}$H$_{51}$ClN$_2$OS |
| 7 | n-dodecyl | C$_{18}$H$_{37}$ | H | 86 | 69 | C$_{34}$H$_{68}$N$_2$OS |
| 8 | cyclohexyl | C$_{18}$H$_{31}$ | H | 60 | 75 | C$_{28}$H$_{54}$N$_2$OS |
| 9 | benzyl | C$_{18}$H$_{37}$ | H | 80 | 81 | C$_{29}$H$_{50}$N$_2$OS |
| 10 | 3-indolyl | C$_{18}$H$_{37}$ | H | 125 | 65 | C$_{30}$H$_{49}$N$_3$OS |
| 11 | 3-pyridinyl | C$_{18}$H$_{37}$ | H | 94 | 63 | C$_{27}$H$_{47}$N$_3$OS |
| 12-HCl | 3-furanyl | C$_{18}$H$_{37}$ | H | 99 | 60 | C$_{26}$H$_{47}$ClN$_2$O$_2$S |
| 13 | 4-dimethylaminophenyl | C$_{18}$H$_{37}$ | H | 75 | 75 | C$_{30}$H$_{53}$N$_3$OS |
| 14 | 3-hydroxyphenyl | C$_{18}$H$_{37}$ | H | 50 | 69 | C$_{28}$H$_{48}$N$_2$O$_2$S |
| 15-HCl | 4-methoxyphenyl | C$_{18}$H$_{37}$ | H | 95 | 70 | C$_{29}$H$_{51}$ClN$_2$O$_2$S |
| 16-HCl | 3,4-dimethoxyphenyl | C$_{18}$H$_{37}$ | H | 103 | 83 | C$_{30}$H$_{53}$ClN$_2$O$_3$S |
| 17-HCl | 3,4,5-trimethoxyphenyl | C$_{18}$H$_{37}$ | H | 115 | 70 | C$_{31}$H$_{55}$ClN$_2$O$_4$S |
| 18-HCl | 4-acetamidophenyl | C$_{18}$H$_{37}$ | H | 170 | 63 | C$_{30}$H$_{52}$ClN$_3$O$_2$S |
| 19 | 4-fluorophenyl | C$_{18}$H$_{37}$ | H | 65 | 73 | C$_{28}$H$_{47}$FN$_2$OS |
| 20 | 4-bromophenyl | C$_{18}$H$_{37}$ | H | 81 | 77 | C$_{28}$H$_{47}$BrN$_2$OS |
| 21 | 4-nitrophenyl | C$_{18}$H$_{37}$ | H | 115 | 60 | C$_{28}$H$_{47}$N$_3$O$_3$S |
| 22 | 4-cyanophenyl | C$_{18}$H$_{37}$ | H | 90 | 70 | C$_{29}$H$_{47}$N$_3$OS |

TABLE 1-continued

Structures and Physical Data of Synthesized Compounds

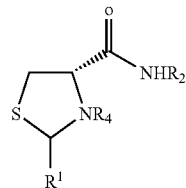

| compound | R¹ | R² | R⁴ | mp (° C.) | yield (%) | formula |
|---|---|---|---|---|---|---|
| 23 | 3,5-difluorophenyl | $C_{18}H_{37}$ | H | 113 | 70 | $C_{28}H_{46}F_2N_2OS$ |
| 24 | 2,6-dichlorophenyl | $C_{18}H_{37}$ | H | 49 | 80 | $C_{28}H_{46}Cl_2N_2OS$ |
| 25 | 3-bromo-4-fluorophenyl | $C_{18}H_{37}$ | H | 100 | 78 | $C_{29}H_{46}BrFN_2OS$ |
| 26 | 4-methylphenyl | $C_{18}H_{37}$ | H | 120 | 73 | $C_{29}H_{50}N_2OS$ |
| 27-HCl | biphenyl | $C_{18}H_{37}$ | H | 130 | 70 | $C_{34}H_{53}ClN_2OS$ |
| 28 | phenyl | $C_{18}H_{37}$ | $COCH_3$ | 90 | 95 | $C_{30}H_{50}N_2O_2S$ |
| 29 | phenyl | $C_{18}H_{37}$ | $SO_2Me$ | 55 | 90 | $C_{29}H_{50}N_2O_3S_2$ |

Example 4

Analysis of Selected Prostate Cancer Cell Lines by RT-PCR for LPA Receptor Expression DU-145, PC-3, and LNCaP human prostate cancer cells, and RH7777 rat hepatoma cells were obtained from American Type Culture Collection (Manassas, Va.). Dr. Mitchell Steiner at University of Tennessee Health Science Center, kindly provided PPC-1 and TSU-Pr1 cells. Prostate cancer cells and RH7777 cells were maintained in RPMI 1640 medium and DMEM (Mediatech, Inc., Herndon, Va.), respectively, supplemented with 10% fetal bovine serum (Gibco, Grand Island, N.Y.) in 5% $CO_2$/95% air humidified atmosphere at 37° C.

Total RNA was extracted using TRIzol® reagent (Invitrogen Corp., Carlsbad, Calif.) according to the manufacturer's instruction. 0.5 µg ($LPA_1$) or 1 µg ($LPA_2$ and $LPA_3$) of total RNA was used to perform RT-PCR using Super-Script™ One-Step RT-PCR with Platinum® Taq (Invitrogen Corp., Carlsbad, Calif.) with 0.2 µM of primers. The following primer pairs were used:

```
LPA₁ forward
5'-GCTCCACACACGGATGAGCAACC-3',    (SEQ ID NO:1)
and

LPA₁ reverse
5'-GTGGTCATTGCTGTGAACTCCAGC-3';   (SEQ ID NO:2)

LPA₂ forward
5'-CTGCTCAGCCGCTCCTATTTG-3',      (SEQ ID NO:3)
and

LPA₂ reverse
5'-AGGAGCACCCACAAGTCATCAG-3';     (SEQ ID NO:4)

LPA₃ forward
5'-CCATAGCAACCTGACCAAAAAGAG-3',   (SEQ ID NO:5)
and

LPA₃ reverse
5'-TCCTTGTAGGAGTAGATGATGGGG-3';   (SEQ ID NO:6)

β-actin forward
5'-GCTCGTCGTCGACAACGGCTC-3',      (SEQ ID NO:7)
and

β-actin reverse
5'-CAAACATGATCTGGGTCATCTTCTC-3'.  (SEQ ID NO:8)
```

PCR conditions were as follows: After 2 min denaturation step at 94° C., samples were subjected to 34 to 40 cycles at 94° C. for 30 sec, 60° C. ($LPA_1$) or 58° C. ($LPA_2$ and $LPA_3$) for 30 sec, and 72° C. for 1 min, followed by an additional elongation step at 72° C. for 7 min. Primers were selected to span at least one intron of the genomic sequence to detect genomic DNA contamination. The PCR products were separated on 1.5% agarose gels, stained with ethidium bromide, and the band intensity was quantified using Quantity One Software (Bio-Rad Laboratories, Inc., Hercules, Calif.). Expression levels of each receptor subtype in different cell lines were expressed as ratios compared to β-actin mRNA level.

LPL receptor expression in these cell lines was determined to validate their use as in vitro models (see Table 2 below). 1 µg of total RNA was subjected to RT-PCR, the PCR products were separated on agarose gels, and relative expression level of each receptor subtype compared to β-actin was quantified by Quantity One Software (Bio-Rad). $LPA_1$ was the predominant LPL receptor expressed in these cell lines. However, LNCaP cells did not express this receptor subtype. $LPA_3$ receptor was uniquely expressed in prostate cancer cell lines. RH7777 cells do not express any of the known LPL receptors.

TABLE 2

LPL Receptor mRNA Expression

| LPL Receptor | Old name | Expression level relative to β-actin | | | | | |
|---|---|---|---|---|---|---|---|
| | | RH7777 | DU145 | PC-3 | LNCaP | PPC-1 | TSU-Pr1 |
| $LPA_1$ | EDG-2 | UD[a] | 2.16 | 2.53 | UD | 2.29 | 2.13 |
| $LPA_2$ | EDG-4 | UD | 0.33 | 0.43 | 0.32 | 0.41 | 0.19 |
| $LPA_3$ | EDG-7 | UD | 0.07 | 0.27 | 0.28 | 0.15 | UD |
| Sum $LPA_{1-3}$ | | 0 | 2.56 | 3.23 | 0.60 | 2.85 | 2.32 |

[a]UD = under detection limit

Example 5

Cytotoxicity Assay in Prostate Cancer Cells

For in vitro cytotoxicity screening, 1000 to 5000 cells were plated into each well of 96-well plates depending on growth rate, and exposed to different concentrations of a test compound for 96 h in three to five replicates. All the compounds were dissolved in dimethyl sulfoxide at 5 to 20 mM, and diluted to desired concentrations in complete culture medium. Cell numbers at the end of the drug treatment were measured by the SRB assay (Gududuru et al., "Synthesis and Biological Evaluation of Novel Cytotoxic Phospholipids for Prostate Cancer," *Bioorg. Med. Chem. Lett.* 14:4919-4923 (2004); Rubinstein et al., "Comparison of in vitro Anticancer-Drug-Screening Data Generated with a Tetrazolium Assay Versus a Protein Assay Against a Diverse Panel of Human Tumor Cell Lines," *J. Natl. Cancer Inst.* 82:1113-1118 (1990), each of which is hereby incorporated by reference in its entirety). Briefly, the cells were fixed with 10% of trichloroacetic acid, stained with 0.4% SRB, and the absorbances at 540 nm was measured using a plate reader (DYNEX Technologies, Chantilly, Va.). Percentages of cell survival versus drug concentrations were plotted and the $IC_{50}$ (concentration that inhibited cell growth by 50% of untreated control) values were obtained by nonlinear regression analysis using WinNonlin (Pharsight Corporation, Mountain View, Calif.). 5-fluorouracil was used as a positive control to compare potencies of the new compounds.

A sandwich ELISA (Roche, Mannheim, Germany) utilizing monoclonal antibodies specific for DNA and histones was used to quantify degree of apoptosis induced by the analogs after 72 h exposure. This assay measures DNA-histone complexes (mono- and oligonucleosomes) released into cytoplasm from the nucleus during apoptosis. RH7777 cells were employed because of nonspecific cytotoxicity of compound 4 in receptor-negative cells as well as receptor-positive prostate cancer cells.

The ability of 2-aryl-thiazolidine derivatives (ATCAAS) to inhibit the growth of five human prostate cancer cell lines (DU-145, PC-3, LNCaP, PPC-1, and TSU-Pr1) was assessed using the sulforhodamine B (SRB) assay (described above). A control cell line (RH7777) that does not express LPL receptors (Svetlov et al., "EDG Receptors and Hepatic Pathophysiology of LPA and SIP: EDG-ology of Liver Injury," *Biochimica et Biophysica ACT* 1582:251-256 (2002), which is hereby incorporated by reference in its entirety) was also utilized to understand whether the antiproliferative activity of these derivatives is mediated through inhibition of LPL receptors.

The diastereomeric mixtures of the target compounds 3-29 were used as such to evaluate their in vitro inhibitory activity against prostate cancer cell lines, and the results are summarized in Tables 3 and 4 below. 5-Fluorouracil was used as the reference drug. To deduce sound structure-activity relationships, $IC_{50}$s should on principle be determined on pure isomers. One drawback of testing mixtures of stereoisomers, unavoidable in this case, was that the effect of each stereoisomer on the biological activity could not be assessed. On the other hand, the $IC_{50}$ values calculated can be used as a screening method to select promising selective cytotoxic agents and to identify the diastereomeric mixture with the best availability to inhibit the growth of prostate cancer cells. Many of these thiazolidine analogs were very effective in killing prostate cancer cell lines with $IC_{50}$ values in the low/sub micromolar range (Table 3). Examination of the cytotoxic effects of compounds 3-5 shows that as the chain length increases from $C_7$ to $C_{18}$, the potency also increases. However, a further increase in the alkyl chain length by one carbon unit (i.e., $C_{18}$ to $C_{19}$) caused a significant loss in cytotoxicity. Interestingly, $C_{14}$ derivative (compound 4) demonstrated higher potency than compound 5, but was 8-fold less selective against RH7777 cell line. Thus, an alkyl chain with a $C_{18}$ unit is optimal for maintaining the potency and selectivity observed in this series of compounds. N-Acyl and N-sulfonyl derivatives (compounds 28 and 29) were less cytotoxic than parent compound 5. Replacement of the phenyl ring with an alkyl or cyclohexyl group reduced the potency (compounds 7 and 8) relative to the thiazolidine (compound 5) derivative. Introduction of a methylene spacer separating the phenyl ring and the thiazolidine ring furnished a compound 9, which was less active than the parent compound 5.

TABLE 3

Antiproliferative effects of compounds 3-17 on prostate cancer cell lines

| | $IC_{50}$ (μM) | | | | | |
|---|---|---|---|---|---|---|
| Compd | RH7777[a] | DU-145[b] | PC-3[b] | LNCaP[b] | PPC-1[b] | TSU-Pr1[b] |
| 3.HCl | 52.2 | 44.9 | 38.5 | 12.4 | 34.7 | 28.0 |
| 4.HCl | 3.4 | 2.4 | 3.0 | 1.4 | 1.3 | 2.0 |
| 5.HCl | 25.6 | 5.4 | 7.8 | 2.1 | 2.0 | 5.0 |
| 6.HCl | NA | >20 | NA | 13.6 | 16.8 | >20 |
| 7 | ~20 | 8.9 | 15.0 | 11.9 | 13.0 | 10.7 |
| 8 | >20 | >20 | >20 | 12.8 | 9.3 | >20 |
| 9 | >20 | 15.3 | 16.4 | 4.4 | 4.0 | 11.2 |
| 10 | >20 | 8.9 | 11.5 | 2.1 | 1.3 | 4.4 |
| 11 | 10.5 | 7.5 | 9.2 | 3.6 | 2.9 | 7.8 |
| 12.HCl | 10.4 | 6.6 | 8.1 | 1.7 | 1.1 | 4.2 |
| 13 | >20 | 5.3 | 6.0 | 1.6 | 1.1 | 3.0 |
| 14 | 31.0 | 5.7 | 6.7 | 1.7 | 1.2 | 4.0 |

TABLE 3-continued

Antiproliferative effects of compounds
3-17 on prostate cancer cell lines

| | IC$_{50}$ (µM) | | | | |
|---|---|---|---|---|---|
| Compd | RH7777[a] | DU-145[b] | PC-3[b] | LNCaP[b] | PPC-1[b] | TSU-Pr1[b] |
| 15.HCl | >20 | 8.7 | ~20 | 2.1 | 1.5 | ND |
| 16.HCl | 10.3 | 4.5 | 5.2 | 0.85 | 0.58 | 2.4 |
| 17.HCl | 11.4 | 3.9 | 4.0 | 0.82 | 0.48 | 2.4 |
| 5-FU | ND | 11.9 | 12.0 | 4.9 | 6.4 | 3.6 |

[a]Control cell line.
[b]Prostate cancer cell lines.
ND = not detectable.
NA = no activity.

TABLE 4

Antiproliferative effects of compounds 18-29
and 34 on prostate cancer cell lines

| | IC$_{50}$ (µM) | | | | |
|---|---|---|---|---|---|
| Compd | RH7777[a] | DU-145[b] | PC-3[b] | LNCaP[b] | PPC-1[b] | TSU-Pr1[b] |
| 18.HCl | 21.1 | 3.1 | 5.6 | 1.3 | 0.55 | 0.94 |
| 19 | 17.4 | 5.7 | 6.8 | 1.9 | 2.1 | 5.4 |
| 20 | >20 | 13.8 | 17.3 | 5.1 | 3.7 | 18.3 |
| 21 | ~20 | 15.3 | ~20 | 8.4 | 15.3 | 15.9 |
| 22 | >20 | >20 | >20 | 5.9 | 5.0 | >20 |
| 23 | >20 | >20 | >20 | 11.2 | 10.6 | >20 |
| 24 | >20 | >20 | >20 | 13.1 | 17.1 | ~20 |
| 25 | ~20 | 11.3 | 13.5 | 3.0 | 4.7 | 14.0 |
| 26 | >20 | 10.5 | 12.8 | 1.9 | 1.9 | 8.0 |
| 27.HCl | >20 | >20 | >20 | >20 | >20 | >20 |
| 28 | >20 | ~20 | ~20 | 16.1 | 12.6 | >20 |
| 29 | >20 | >20 | >20 | >20 | >20 | >20 |
| 34 | >20 | >20 | >20 | >20 | >20 | >20 |
| 5-FU | ND | 11.9 | 12.0 | 4.9 | 6.4 | 3.6 |

[a]Control cell line.
[b]Prostate cancer cell lines.

To understand the effect of unsaturation on potency and selectivity, and to overcome the problems associated with stereoisomers, the central thiazolidine core in compound 5 was replaced with a thiazole ring. However, thiazole derivative (compound 34) did not show any activity below 20 µM in both prostate and RH7777 cells, which indicates that thiazolidine ring with two chiral centers plays an important role in providing potency and selectivity. Replacements of the phenyl ring with a heterocycle, such as an indole, pyridine or furan ring was investigated by synthesizing analogs (compounds 10-12). The furanyl derivative (compound 12) showed equivalent cytotoxicity as compound 5, but was 3-fold less selective against RH7777 cells.

The cytotoxicity data of compounds 13-27 provides a summary of a broad survey of phenyl ring substituted analogs. Examination of the IC$_{50}$ values of these analogs demonstrates a greater tolerance for diverse substituents in the phenyl ring. In general, the most potent analogues possessed electron-donating substituents, as exemplified by comparison of compound 13, and compounds 16-18, relative to compound 5. One of the most active compounds (compound 18) with an IC$_{50}$ of 0.55 µM was 38-fold more selective in PPC-1 cells compared to RH7777 cells. On the other hand, thiazolidine analogs (compounds 19-25), with electron-withdrawing substituents demonstrated less cytotoxicity. Comparison of the potencies of compound 26 and compound 27, suggest that substitution of the phenyl ring with a bulky group reduces the activity.

From the LPL receptor mRNA expression studies (Table 2), it was evident that these cell lines serve as an excellent model system to explore the effects of LPL receptor. Given the structural similarity of SAPs to ceramide (and the known ability of ceramide to induce apoptosis), it was then determined whether the antiproliferative effects of thiazolidine analogs were mediated via apoptotic events. The ability of the analogs to induce apoptosis in LNCaP, PC-3, and RH7777 cells was examined using a quantitative sandwich ELISA that measures DNA-histone complex released during apoptosis. The enrichment factor calculated (as ratio of OD405 in treated and un-treated cells) provides a quantitative assessment of the degree of apoptosis induced. Initially, only two compounds (4 & 5) were used for this study. Apoptotic activity of analog (compound 4) was selective in prostate cancer cells despite nonselective cytotoxicity in RH7777 negative control cells (see Table 5 below). Analog compound 5 induced apoptosis in PC-3 and LNCaP cells, but to a lesser extent in PC-3 cells perhaps due to lower potency in this cell line. This data suggests that thiazolidine analogs may act as potent inducers of apoptosis and selectively kill a variety of prostate cancer cell lines.

TABLE 5

Thiazolidine Amides-Induced Apoptosis

| Compound for 72 h | | PC-3 | LNCaP | RH7777 |
|---|---|---|---|---|
| 4 | 2 µM | 1.8 | 14.1 | 2.6 |
| | 5 µM | 18.7 | 75.4 | 3.2 |
| | 10 µM | 54.0 | 80.7 | 2.5 |
| 5 | 2 µM | 1.4 | 4.5 | |
| | 5 µM | 2.3 | 45.2 | ND |
| | 10 µM | 3.4 | 37.1 | |
| | 20 µM | 12.7 | 26.1 | |

Figures 4A, 4B:
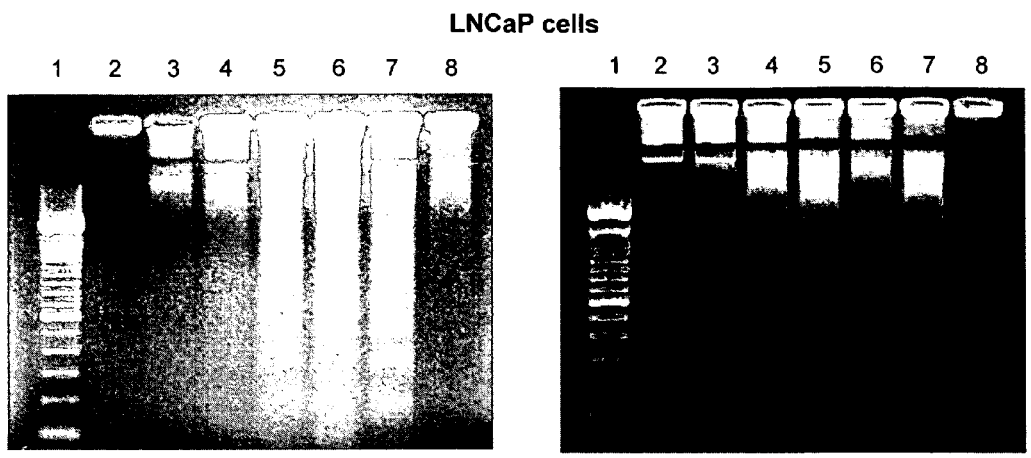
FIGS. 4A-B illustrate agarose gel electrophoresis of total DNA extracted from 2×10⁶ LNCaP cells following treatment with thiazolidine compounds 4 (FIG. 4A) and 5 (FIG. 4B) for 24 to 108 hours. The results show the effects of treatment on DNA fragmentation, indicating progression of cell death.

These results are consistent with the assay testing LNCaP cells for DNA fragmentation by agarose gel electrophoresis. LNCaP cells were treated with a thiazolidine derivative (compound 4 or 5) for 24 to 108 hours, and then total DNA was extracted from 2×10$^6$ cells by simple centrifugation method, treated with RNase and Proteinase K. After precipication in ethanol, DNA was reconstituted in Tris-EDTA buffer, separated on agarose gels, and visualized by ethidium bromide staining (Herrmann et al., "A Rapid and Simple Method for the Isolation of Apoptotic DNA Fragments," Nucl. Acids Res. 22:5506-5507 (1994), which is hereby incorporated by reference in its entirety). The results, shown in FIGS. 4A-B, demonstrate that both of these compounds induce cell apoptosis in the LNCaP prostate cancer cell line.

Figure 5A:
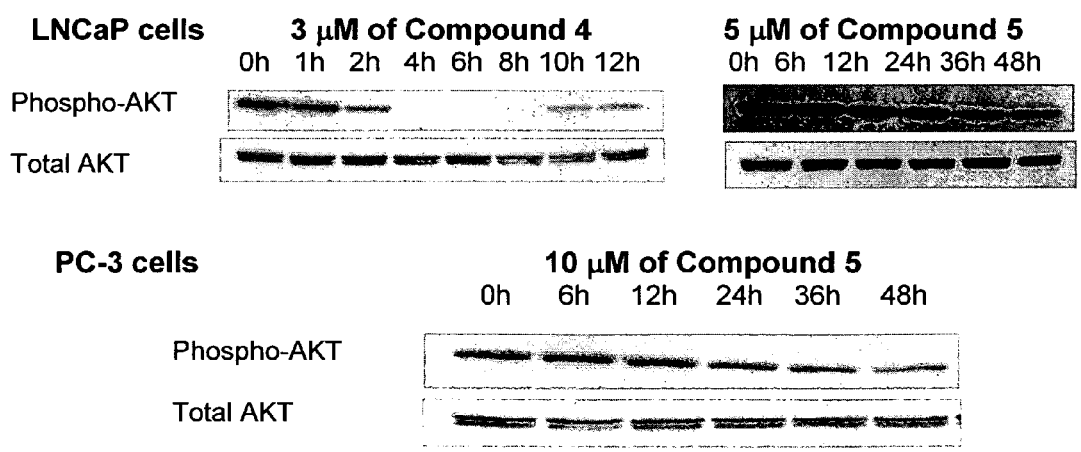
FIGS. 5A-B demonstrate AKT inhibitory effects of thiazolidine compounds, as measured by inhibition of AKT phosphorylation.
Figure 5B:
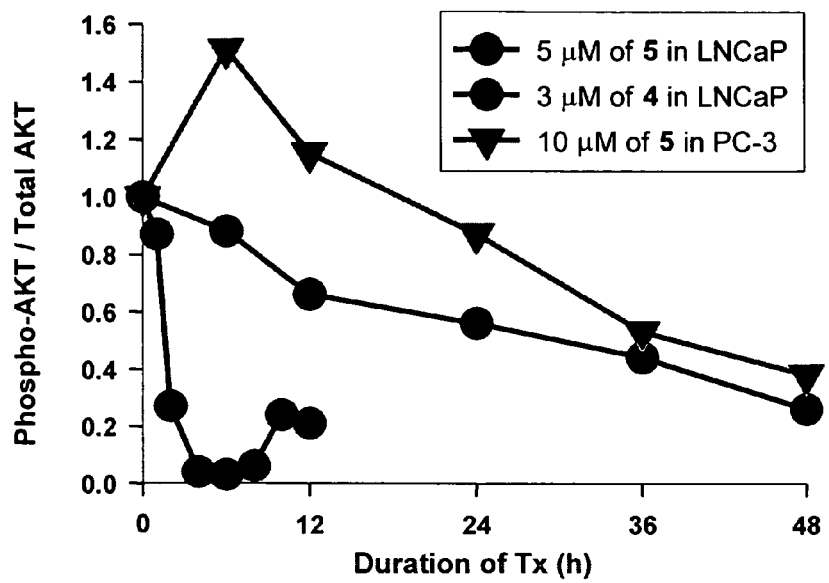

As another assessment of cytotoxicity, AKT inhibition was measured. 30 µg of total cellular protein from untreated control cells and compound-treated cells were separated by SDS-PAGE, transferred to nitrocellulose membrane, and total AKT and phospho-AKT were probed with anti-AKT and anti-phospho AKT antibody specific for AKT phosphorylated at Ser 473, respectively (Cell Signaling Technology, Beverly, Mass.). The immunoblots were visualized by enhanced chemiluminescence, and changes of relative levels of phospho-AKT compared to total AKT by analog treatment were quantified by densitometric analysis. FIG. 5B graphically illustrates the immunological detection of AKT using anti-AKT and anti-phospo-AKT, shown in FIG. 5A.

From the foregoing, it should be appreciated that the introduction of ring activating groups on the phenyl ring resulted in increasing potencies for prostate cancer cell lines. The above results demonstrate several new anticancer agents (represented by compounds 16, 17, and 18) with low/sub micromolar cytoxicity and high selectivity. From this study, compound 18 emerged as one of the most potent and selective cytotoxic agents with an $IC_{50}$ of 0.55 μM and 38-fold selectivity in PPC-1 cells. Further, the ability of these analogs to induce apoptosis in LNCaP, PC-3 and RH7777 cells provides an important clue to understand their mechanism of action.

Example 6

Synthesis of Thiazolidinone Amides

The synthesis of thiazolidinone derivatives (compounds 65-72) utilized straightforward chemistry as shown in scheme 4 (FIG. 6), where 1 is 1. Various 4-thiazolidinones were synthesized following a reported procedure of condensing mercaptoacetic acid, glycine methyl ester, and aromatic aldehydes in a one-pot reaction, followed by basic hydrolysis of the ester (Holmes et al., "Strategies for Combinatorial Organic Synthesis: Solution and Polymer-supported Synthesis of 4-thiazolidinones and 4-metathiazanones Derived from Amino Acids," *J. Org. Chem.* 60:7328-7333 (1995), which is hereby incorporated by reference in its entirety). Thiazolidinone amides were obtained by the treatment with appropriate amines in the presence of EDC/HOBt under standard conditions. Compound 65 that has no side chain was synthesized from the corresponding acid as shown in FIG. 6 (scheme 4). Thiazolidinone amides (compounds 73-77) were synthesized by a simple and direct method (Schuemacher et al., "Condensation Between Isocyanates and Carboxylic Acids in the Presence of 4-dimethylaminopyridine (DMAP), a Mild and Efficient Synthesis of Amides," *Synthesis* 22:243-246 (2001), which is hereby incorporated by reference in its entirety), which involves reaction of the acid compound 64a with different isocyanates in the presence of a catalytic amount of DMAP (FIG. 7) (scheme 5). Exhaustive reduction of compound 68 using $BH_3.THF$ under reflux conditions gave compound 79 (FIG. 8) (scheme 6). Oxidation of 68 using $H_2O_2$ and with $KMnO_4$ afforded sulfoxide (compound 80) and sulfone (compound 81), respectively, as shown in scheme 6. All compounds were characterized by $^1H$ and $^{13}C$ NMR, mass spectroscopy and, in certain cases, elemental analysis.

Compounds were obtained as mixtures of diastereomers and were used as such for the biological studies. Characteristic data for exemplary compounds 68, 71, 72, and 81 are provided below.

N-octadecyl-2-(4-oxo-2-phenylthiazolidin-3-yl)acetamide (compound 68): $^1H$ NMR (300 MHz, $CDCl_3$): δ 0.89 (t, J=6.0 Hz, 3H), 1.26 (br s, 30H), 1.46 (m, 2H), 3.16-3.29 (m, 3H), 3.82 (d, J=1.5 Hz, 2H), 4.20 (s, 0.5H), 4.25 (s, 0.5H), 5.83-5.85 (m, 2H), 7.27-7.41 (m, 5H); $^{13}C$ NMR (300 MHz, $CDCl_3$): δ 13.55, 22.13, 26.30, 28.69, 28.80, 28.88, 28.99, 29.03, 29.10, 29.14, 31.37, 32.13, 39.08, 45.88, 63.67, 127.05, 128.58, 128.96, 137.61, 166.30, 171.61; MS (ESI) m/z 511 [M+Na]. Anal. Calcd for $C_{29}H_{48}N_2O_2S$: C, 71.26; H, 9.90; N, 5.73. Found: C, 71.18; H, 10.03; N, 5.79.

2-(2-(4-methoxyphenyl)-4-oxothiazolidin-3-yl)-N-octadecylacetamide (compound 71): $^1H$ NMR (300 MHz, $CDCl_3$): δ 0.89 (t, J=6.0 Hz, 3H), 1.26 (br s, 30H), 1.33 (s, 2H), 3.16-3.19 (m, 1H), 3.2-3.29 (m, 2H), 3.80 (d, J=0.9 Hz, 2H), 3.83 (s, 3H), 4.16 (s, 0.5H), 4.21 (s, 0.47H), 5.82 (s, 1H), 6.9 (dd, J=1.8 Hz, 2H), 7.29 (dd, J=1.5 Hz, 2H); $^{13}C$ NMR (300 MHz, $CDCl_3$): δ 13.53, 22.12, 26.31, 28.70, 28.74, 28.79, 28.89, 28.99, 29.03, 29.09, 29.13, 31.36, 32.23, 39.06, 45.74, 54.79, 63.44, 128.64, 129.11, 159.97, 166.41, 171.47; MS (ESI) m/z 541 [M+Na]. Anal. Calcd for $C_{30}H_{50}N_2O_3S$: C, 69.45; H, 9.71; N, 5.40. Found: C, 69.30; H, 9.86; N, 5.43.

2-(2-(2,6-dichlorophenyl)-4-oxothiazolidin-3-yl)-N-octadecylacetamide (compound 72): $^1H$ NMR (300 MHz, $CDCl_3$): δ 3.54 (d, J=15.3 Hz, 1H), 3.87 (s, 2H), 4.25 (d, J=15.3 Hz, 1H), 5.88 (s, 1H), 7.10 (t, J=1.8 Hz, 1H), 7.36-7.43 (m, 7H), 8.29 (s, 1H); $^{13}C$ NMR (300 MHz, $CDCl_3$): δ 32.35, 46.73, 64.40, 117.37, 123.85, 127.29, 128.74, 129.32, 134.59, 136.87, 138.61, 165.14, 172.60; MS (ESI) m/z 403 [M+Na]. Anal. Calcd for $C_{17}H_{14}Cl_2N_2O_2S$: C, 53.55; H, 3.70; N, 7.35. Found: C, 53.39; H, 3.47; N, 7.36.

N-octadecyl-2-(4-oxo-2-phenyl-1-sulfonyl-thiazolidin-3-yl)acetamide (compound 81): $^1H$ NMR (300 MHz, $CDCl_3$): δ 0.89 (t, J=6.0 Hz, 3H), 1.26 (br s, 32H), 3.19-3.34 (m, 3H), 3.88-4.03 (dd, J=16.5 Hz, 2H), 4.66 (s, 0.5H), 4.72 (s, 0.5H), 5.67 (br s, 1H), 5.95 (s, 1H), 7.38 (m, 2H), 7.50-7.53 (m, 3H); $^{13}C$ NMR (300 MHz, $CDCl_3$): δ 13.54, 22.12, 26.26, 28.66, 28.79, 28.96, 29.02, 29.09, 29.14, 31.36, 39.30, 44.35, 49.85, 81.32, 125.77, 128.43, 128.91, 130.55, 163.23, 165.30; MS (ESI) m/z 519 [M−H]. Anal. Calcd for $C_{29}H_{48}N_2O_4S$: C, 66.88; H, 9.29; N, 5.38. Found: C, 66.68; H, 9.27; N, 5.41.

Example 7

Cytotoxicity Assay

The antiproliferative activity of all the synthesized compounds was evaluated against five human prostate cancer cell lines and in RH7777 cells (negative control) using the sulforhodamine B (SRB) assay (see description in Example 5 above). 5-Fluorouracil (5-FU) was used as reference drug. As shown in Table 6, 4-thiazolidinone carboxylic acids (compounds 64a and 64b) were unable to inhibit the growth of any of the five prostate cancer cells below 50 μM. However, the corresponding amides (compounds 66-68) showed higher activities. It was observed that an increase in the alkyl chain length [compounds 66 (C10), 67 (C14), and 68 (C18)] enhances the antiproliferative activity of these analogs in prostate cancer cells. Interestingly, the simple amide 65 without any long alkyl chain is not cytotoxic below 100 μM, which indicates that the absence of an alkyl side chain causes a considerable decrease in antiproliferative effect. On the other hand, replacement of the alkyl chain with various aryl side chains (compounds 73-78) reduced the biological activity. Among this series, compound 73 is moderately cytotoxic, where as analogs (compounds 76-78) displayed poor cytotoxicity in several prostate cancer cell lines. However, it is noteworthy to mention that thiazolidinone amides (compounds 74 and 75), with electron-withdrawing substituents on the aryl ring showed cytotoxicity in the range of 13-29 μM against all five prostate cancer cell lines.

TABLE 6

Antiproliferative effects of compounds 64a-64b and 65-78

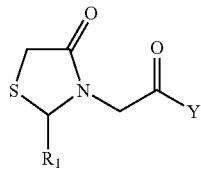

| Cmpd | $R^1$ | Y | RH7777[a] | DU-145[b] | PC-3[b] | LNCaP[b] | PPC-1[b] | TSU[b] |
|---|---|---|---|---|---|---|---|---|
| | | | | IC$_{50}$ (µM) | | | | |
| 64a | phenyl | OH | ND | >50 | >50 | >50 | >50 | >50 |
| 64b | biphenyl | OH | >100 | >100 | >100 | >100 | >100 | >100 |
| 65 | phenyl | NH$_2$ | >100 | >100 | >100 | >100 | >100 | >100 |
| 66 | phenyl | NH—C$_{10}$H$_{21}$ | 20.0 | 22.4 | 20.3 | 14.1 | 15.8 | 19.7 |
| 67 | phenyl | NH—C$_{14}$H$_{29}$ | 16.4 | 19.6 | 13.5 | 14.1 | 10.1 | 13.4 |
| 68 | phenyl | NH—C$_{18}$H$_{37}$ | 39.6 | 12.6 | 11.1 | 9.3 | 7.1 | 8.5 |
| 69 | biphenyl | NH—C$_{18}$H$_{37}$ | >50 | >50 | >50 | >50 | >50 | >50 |
| 70 | dimethylamino naphthalen-4-yl | NH—C$_{18}$H$_{37}$ | >50 | >50 | >50 | >50 | >50 | >50 |
| 71 | 4-methoxy phenyl | NH—C$_{18}$H$_{37}$ | 31.1 | 14.8 | 12.6 | 11.8 | 10.7 | 17.5 |
| 72 | 2,6-dichloro phenyl | NH—C$_{18}$H$_{37}$ | >50 | >50 | >50 | >50 | >50 | >50 |
| 73 | phenyl | NH-3,5-difluoro phenyl | 70.9 | 69.0 | 74.1 | 24.1 | 46.2 | 53.2 |
| 74 | phenyl | NH-3,5-di(trifluoromethyl) phenyl | 25.4 | 16.2 | 18.1 | 14.5 | 13.1 | 16.1 |
| 75 | phenyl | NH-3,5-di chlorophenyl | 34.9 | 24.0 | 28.6 | 13.2 | 20.5 | 17.2 |
| 76 | phenyl | NH-2,4-dimethoxy phenyl | >100 | >100 | >100 | 82.5 | >100 | 60.8 |
| 77 | phenyl | NH-naphthyl | >100 | >100 | >100 | 31.4 | >100 | 69.9 |
| 78 | phenyl | 2,4dimethoxy phenylethyl | >100 | >100 | >100 | >100 | >100 | >100 |
| 5-FU | | | ND | 11.9 | 12.0 | 4.9 | 6.4 | 3.6 |

[a]Control cell line;
[b]Prostate cancer cell lines.

TABLE 7

Antiproliferative effects of compounds 79-81

| Cmpd | RH7777[a] | DU-145[b] | PC-3[b] | LNCaP[b] | ppc-1[b] | TSU[b] |
|---|---|---|---|---|---|---|
| | | | IC$_{50}$ (µM) | | | |
| 79 | >20 | 15.8 | >20 | >20 | 12.0 | 6.1 |
| 80 | 11.5 | 11.2 | 6.5 | 7.9 | 5.4 | 6.4 |
| 81 | 22.1 | 15.5 | 8.5 | 10.9 | 5.5 | 9.3 |
| 5-FU | ND | 11.9 | 12.0 | 4.9 | 6.4 | 3.6 |

[a]Control cell line;
[b]Prostate cancer cell lines.

Thiazolidinone derivatives (compounds 69 and 70) with bulky biphenyl or naphthalene groups demonstrated low cytotoxicity compared to compound 68 (Table 6). Compounds 71 and 72 were synthesized to understand the effects of aromatic ring substitution in compound 68. It was observed that electron-donating substituents maintained good activity while the ortho electron-withdrawing substituents substantially decrease the antiproliferative activity of these derivatives (Table 6). Compound 79, which has no amide groups, showed significantly good potency in all five prostate cancer cell lines. Notably, compounds 80 and 81 bearing sulfoxide or sulfone moiety displayed higher cytotoxic potency comparable to that of the reference drug 5-FU against both PC-3 and PPC-1 cell lines (Table 7).

In summary, a series of novel and cytotoxic 4-thiazolidinone amides were prepared and identified. Among this series, detailed structure activity relationship studies of type I compounds (FIG. 6) were performed to evaluate their antiproliferative activity against five prostate cancer cell lines and RH7777 cells (negative controls). The cytotoxicity study shows that the antiproliferative activity is sensitive to 2-aryl ring substitutions, the length of the alkyl side chain, and the removal or replacements of the lipophilic alkyl side chain. Sulfur oxidation is well tolerated as compounds 80 and 81 showed significant cytotoxicity compared to 5-FU. This study resulted in the discovery of potent cytotoxic 4-thiazolidinones (compounds 68, 80, and 81), which inhibit the growth of all five human prostate cancer cell lines (DU-145, PC-3, LNCaP, PPC-1, and TSU) with 2-5-fold lower selectivity compared to RH7777 cell line. These 4-thiazolidinone derivatives are a significant improvement on the SAP moiety in that they are less cytotoxic but demonstrated improved selectivity in non-tumor cells.

Example 8

Cytotoxicity Assay in Breast and Ovarian Cancer Cells

The most potent compounds from each structural formula were selected and tested for their growth inhibitory activity in a human breast cancer cell line (MCF-7) and three human ovarian cancer cell lines (CHO-1, CaOv-3, SKOv-3, and OVCAR-3). In vitro cytotoxicity assay was performed by the same sulforhodamine B (SRB) assay (described above). The compounds shown in Table 8 below where tested for activity against the breast cancer and ovarian cancer cell lines.

TABLE 8

Antiproliferative effects of compounds on breast and ovarian cancer cell lines

| | IC$_{50}$ (µM) | | | | |
|---|---|---|---|---|---|
| Compd | MCF-7[a] | CHO-1[b] | CaOv-3[b] | OVCAR-3[b] | SKOv-3[b] |
| 3.HCl | 50.3 | NT | 19.2 | 34.0 | 47.8 |
| 4.HCl | 4.2 | NT | 13.9 | 1.6 | 2.1 |
| 5.HCl (R) | 4.2 | NT | 2.5 | 4.5 | 8.5 |
| 5.HCl (S) | 7.4 | NT | 18.0 | 5.2 | 18.0 |
| 6.HCl | >20 | NT | NT | NT | NT |
| 7 | 10.4 | NT | NT | NT | NT |
| 8 | ~20 | NT | NT | NT | NT |
| 9 | 18.7 | NT | NT | NT | NT |
| 10 | 10.6 | NT | NT | NT | NT |
| 11 | 9.3 | NT | NT | NT | NT |
| 12 | NT | NT | 7.7 | 2.3 | 5.4 |
| 13 | 13.5 | NT | NT | NT | NT |
| 14.HCl | NT | NT | 18.3 | 8.1 | 11.0 |
| 15.HCl | 16.3 | NT | NT | NT | NT |
| 16.HCl | NT | NT | 5.5 | 1.2 | 3.6 |
| 17.HCl | NT | NT | 4.4 | 1.4 | 2.7 |
| 18.HCl | NT | NT | 4.9 | 2.0 | 2.6 |
| 19 | 8.8 | NT | 5.5 | 2.3 | 4.2 |
| 20 | 16.6 | NT | NT | NT | NT |
| 21 | 15.3 | NT | NT | NT | NT |
| 24 | 17.7 | NT | NT | NT | NT |
| 25 | 15.3 | NT | NT | NT | NT |
| 26 | 10.3 | NT | NT | NT | NT |
| 27.HCl | >20 | NT | NT | NT | NT |
| 28 | 16.3 | NT | NT | NT | NT |
| 29 | >20 | NT | NT | NT | NT |
| 34 | >20 | NT | NT | NT | NT |
| 66 | 13.5 | 21.0 | NT | NT | NT |
| 67 | 8.9 | 11.4 | NT | NT | NT |
| 68 | 15.4 | 23.5 | NT | NT | NT |
| 69 | >20 | >20 | NT | NT | NT |
| 70 | >20 | >20 | NT | NT | NT |
| 71 | 13.0 | 15.2 | NT | NT | NT |
| 72 | ~30 | >30 | NT | NT | NT |
| 80 | 14.3 | 11.6 | NT | NT | NT |
| 81 | 8.9 | 9.8 | NT | NT | NT |

[a]Breast cancer cell line;
[b]Ovarian cancer cell line;
NT = not tested.

Stereoselectivity of compound 5 was observed (compare the (R) and (S) isomers) in CaOV-3 and SKOv-3 cells. Substitutions on 2-phenyl ring generally increased cytotoxicity of the compounds.

Example 9

Synthesis and Testing of Spermine-conjugated Thiazolidine Amide

As illustrated in FIG. 9, a mixture of 4-thiazolidinone acid (where R$^1$ is phenyl and 1 is 1) (1.5 g, 6.32 m mol), 1-(3-dimethylaminopropyl)-3-ethylcarbodiimide hydrochloride (1.51 g, 7.9 m mol) and 1-hydroxybenzotriazole (0.85 g, 6.32 m mol) in CH$_2$Cl$_2$ was cooled in an ice bath was stirred for 10 min. To this solution 4-nitrophenol (0.78 g, 5.61 m mol) was added and stirred for 2 h. The reaction mixture was diluted with CH$_2$Cl$_2$ washed sequentially with cold 5% HCl, saturated NaHCO$_3$, water, brine, dried (anhydrous Na$_2$SO$_4$) and solvent was removed in vacuo. The nitrophenyl ester product (compound 100) was purified by flash chromatography (silica gel) using EtOAc/Hexanes to afford 1.76 g (78%). $^1$HNMR (CDCl$_3$) δ 3.70 (d, J=18 Hz, 1H), 3.85 (d, J=1.2 Hz, 2H), 4.64 (d, J=17.7 Hz, 1H), 5.88 (s, 1H), 7.24 (d, J=2.1 Hz, 1H), 7.26 (d, J=2.4 Hz, 1H), 7.40-7.46 (m, 5H), 8.26 (d, J=1.8 Hz, 1H), 8.28 (d, J=2.1 Hz, 1H).

To a solution of the nitrophenyl ester (compound 100) (0.5 g, 1.39 m mol) in CH$_3$OH (35 mL) at room temperature, a solution of spermine (0.33 g, 1.63 m mol, in CH$_3$OH) was added slowly and stirred for 1 h. The reaction mixture was concentrated in vacuo, and to the concentrated reaction mixture 1:1 (CHCl$_3$:CH$_3$OH) was added and filtered through celite. Solvent was removed in vacuo and the residue was purified by flash column chromatography (silica gel) using CHCl$_3$/CH$_3$OH/i-PrNH$_2$ to give 0.2 g (50%) of spermine conjugate (compound 101), which was converted to the corresponding hydrochloride salt using 2M HCl/Et$_2$O. $^1$HNMR (DMSO-d$_6$) δ 1.71-1.76 (m, 6H), 1.95-2.0 (m, 2H), 2.89-3.0 (m, 10H), 3.0-3.15 (m, 4H), 3.74 (d, J=15.6 Hz, 1H), 3.87 (d, J=15.3 Hz, 1H), 4.10(d, J=16.5 Hz, 1H), 7.35-7.44 (m, 5H), 8.0-8.18 (m, 4H), 8.89 (brs, 2H), 9.15 (brs, 2H). ESIMS m/z 422.4 (M$^+$+1).

Compound 101 demonstrated more potent activity against prostate cancer cells compared to ovarian and MCF-7 breast cancer cells, with IC$_{50}$ (µM) values as follows: RH7777 (>100), DU145 (12.4), PC-3 (11.1), LNCaP (26.2), PPC-1 (11.7), TSU-Pr1 (5.0), MCF-7 (>100), CaOv-3 (39.3), OVCAR-3 (39.7), and SKOv-3 (>100).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A compound according to formula (II)

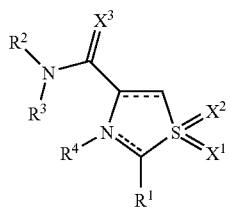

wherein
$X^1$ and $X^2$ are absent;
$X^3$ is oxygen;
$R^1$ is

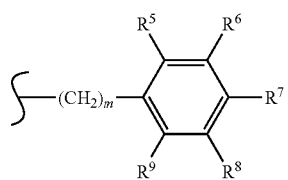

where m is 0;
$R^2$ is an aliphatic, straight-chain C10 to C20 hydrocarbon;
$R^3$ is hydrogen;
$R^4$ is optional, or can be hydrogen, an aliphatic or non-aliphatic straight- or branched-chain C1 to C10 hydrocarbon, acyl, acetyl, or mesyl; and
$R^5$, $R^6$, $R^7$, $R^8$, and $R^9$ are independently selected from the group of hydrogen, hydroxyl, an aliphatic or non-aliphatic straight- or branched-chain C1 to C10 hydrocarbon, alkoxy, nitro, cyano, chloro, fluoro, bromo, iodo, haloalkyl, dihaloalkyl, trihaloalkyl, amino, alkylamino, dialkylamino, acylamino, amido, alkylamido, and dialkylamido.

2. The compound according to claim 1, wherein $R^2$ is a C14 to C18 straight-chain aliphatic hydrocarbon.

3. The compound according to claim 1, wherein $R^1$ is phenyl.

4. The compound according to claim 1, wherein the compound is selected from the group of:
   (4R)-2-(4-methoxyphenyl)-N-octadecylthiazolidine-4-carboxamide,
   (4R)-2-(4-ethoxyphenyl)-N-octadecylthiazolidine-4-carboxamide,
   N-octadecyl-2-phenylthiazole-4-carboxamide,
   (4R)-2-(3,5-difluorophenyl)-N-octadecylthiazolidine-4-carboxamide,
   (4R)-2-(4-cyanophenyl)-N-octadecylthiazolidine-4-carboxamide,
   (4R)-N-octadecyl-2-phenylthiazolidine-4-carboxamide,
   (4S)-N-octadecyl-2-phenylthiazolidine-4-carboxamide,
   (4R)-N-tetradecyl-2-phenylthiazolidine-4-carboxamide,
   (4S)-N-nonadecyl-2-phenylthiazolidine-4-carboxamide,
   (4R)-2-(4-hydroxyphenyl)-N-octadecylthiazolidine-4-carboxamide,
   2-(3-hydroxyphenyl)-N-octadecylthiazolidine-4-carboxamide,
   (4R)-2-(2,4,6-trimethoxyphenyl)-N-octadecylthiazolidine-4-carboxamide,
   2-(3,4-dimethoxyphenyl)-N-octadecylthiazolidine-4-carboxamide,
   2-(3,4,5-trimethoxyphenyl)-N-octadecylthiazolidine-4-carboxamide,
   2-(4-acetamidophenyl)-N-octadecylthiazolidine-4-carboxamide,
   (4R)-2-(4-fluorophenyl)-N-octadecylthiazolidine-4-carboxamide,
   (4R)-2-(2,6-dichlorophenyl)-N-octadecylthiazolidine-4-carboxamide,
   (4R)-2-(4-bromophenyl)-N-octadecylthiazolidine-4-carboxamide,
   (4R)-N-octadecyl-2-p-tolylthiazolidine-4-carboxamide,
   2-(4-nitrophenyl)-N-octadecylthiazolidine-4-carboxamide,
   (4R)-2-(4-(dimethylamino)phenyl)-N-octadecylthiazolidine-4-carboxamide,
   (4R)-2-(3-bromo-4-fluorophenyl)-N-octadecylthiazolidine-4-carboxamide,
   and salts thereof.

5. The compound according to claim 1, wherein the compound is selected from the group of (4R)-N-octadecyl-2-phenylthiazolidine-4-carboxamide,
(4R)-2-(4-(dimethylamino)phenyl)-N-octadecylthiazolidine-4-carboxamide,
2-(3-hydroxyphenyl)-N-octadecylthiazolidine-4-carboxamide,
2-(3,4-dimethoxyphenyl)-N-octadecylthiazolidine-4-carboxamide,
2-(3,4,5-trimethoxyphenyl)-N-octadecylthiazolidine-4-carboxamide,
2-(4-acetamidophenyl)-N-octadecylthiazolidine-4-carboxamide,
(4R)-2-(4-fluorophenyl)-N-octadecylthiazolidine-4-carboxamide, and salts thereof.

6. The compound according to claim 1, wherein the compound is present in a racemic mixture.

7. The compound according to claim 1, wherein the compound is a stereoisomer.

8. The compound according to claim 1, wherein the compound is present in the form of a pharmaceutically acceptable salt.

9. A pharmaceutical composition comprising:
a pharmaceutically acceptable carrier and
a compound according to claim 1.

10. The compound according to claim 1, wherein $R^2$ is a C10 to C20 alkyl group.

11. The compound according to claim 1, wherein $R^2$ is a C10 to C20 alkenyl group.

12. The compound according to claim 1, wherein $R^1$ is 4-methoxyphenyl, 4-ethoxyphenyl, 3,5-difluorophenyl, 4-cyanophenyl, p-tolyl, 4-hydroxyphenyl, 3-hydroxyphenyl, 2,4,6-trimethoxyphenyl, 3,4-dimethoxyphenyl, 3,4,5-trimethoxyphenyl, 4-acetamidophenyl, 4-fluorophenyl, 2,6-dichlorophenyl, 4-bromophenyl, 4-nitrophenyl, 4-(dimethylamino)phenyl, or 3-bromo-4-fluorophenyl.

13. The compound according to claim 1, wherein $R^5$, $R^6$, $R^7$, $R^8$, and $R^9$ are independently selected from the group of hydrogen, hydroxyl, alkoxy, amino, alkylamino, dialkylamino, acylamino, amido, alkylamido, and dialkylamido.

* * * * *

SEQUENCE LISTING

<160> NUMBER OF SEQ ID NOS: 8

<210> SEQ ID NO 1
<211> LENGTH: 23
<212> TYPE: DNA
<213> ORGANISM: artificial
<220> FEATURE:
<223> OTHER INFORMATION: Forward primer for LPA1

<400> SEQUENCE: 1
gctccacaca cggatgagca acc                                                23

<210> SEQ ID NO 2
<211> LENGTH: 24
<212> TYPE: DNA
<213> ORGANISM: artificial
<220> FEATURE:
<223> OTHER INFORMATION: Reverse primer for LPA1

<400> SEQUENCE: 2
gtggtcattg ctgtgaactc cagc                                               24

<210> SEQ ID NO 3
<211> LENGTH: 21
<212> TYPE: DNA
<213> ORGANISM: artificial
<220> FEATURE:
<223> OTHER INFORMATION: Forward primer for LPA2

<400> SEQUENCE: 3
ctgctcagcc gctcctattt g                                                  21

<210> SEQ ID NO 4
<211> LENGTH: 22
<212> TYPE: DNA
<213> ORGANISM: artificial
<220> FEATURE:
<223> OTHER INFORMATION: Reverse primer for LPA2

<400> SEQUENCE: 4
aggagcaccc acaagtcatc ag                                                 22

<210> SEQ ID NO 5
<211> LENGTH: 24
<212> TYPE: DNA
<213> ORGANISM: artificial
<220> FEATURE:
<223> OTHER INFORMATION: Forward primer for LPA3

<400> SEQUENCE: 5
ccatagcaac ctgaccaaaa agag                                               24

<210> SEQ ID NO 6
<211> LENGTH: 24
<212> TYPE: DNA
<213> ORGANISM: artificial
<220> FEATURE:
<223> OTHER INFORMATION: Reverse primer for LPA3

<400> SEQUENCE: 6
tccttgtagg agtagatgat gggg                                               24

<210> SEQ ID NO 7
<211> LENGTH: 21

```
-continued

<212> TYPE: DNA
<213> ORGANISM: artificial
<220> FEATURE:
<223> OTHER INFORMATION: Forward primer for beta-actin

<400> SEQUENCE: 7
gctcgtcgtc gacaacggct c                                              21

<210> SEQ ID NO 8
<211> LENGTH: 27
<212> TYPE: DNA
<213> ORGANISM: artificial
<220> FEATURE:
<223> OTHER INFORMATION: Reverse primer for beta-actin

<400> SEQUENCE: 8
caaacatgat ctgggtcatc ttctcdm                                        27
```